US 9,775,579 B2

(12) United States Patent
Besson

(10) Patent No.: US 9,775,579 B2
(45) Date of Patent: Oct. 3, 2017

(54) MULTI-SOURCE CT SYSTEM AND IMAGING METHOD

(71) Applicant: Guy M. Besson, Broomfield, CO (US)

(72) Inventor: Guy M. Besson, Broomfield, CO (US)

(*) Notice: Subject to any disclaimer, the term of this patent is extended or adjusted under 35 U.S.C. 154(b) by 106 days.

(21) Appl. No.: 15/047,412

(22) Filed: Feb. 18, 2016

(65) Prior Publication Data

US 2016/0235382 A1 Aug. 18, 2016

Related U.S. Application Data

(63) Continuation-in-part of application No. 14/946,626, filed on Nov. 19, 2015.
(Continued)

(51) Int. Cl.
*A61B 6/00* (2006.01)
*A61B 6/03* (2006.01)

(52) U.S. Cl.
CPC .......... *A61B 6/5205* (2013.01); *A61B 6/032* (2013.01); *A61B 6/4007* (2013.01);
(Continued)

(58) Field of Classification Search
None
See application file for complete search history.

(56) References Cited

U.S. PATENT DOCUMENTS 4,064,393 A * 12/1977 Pasedach .............. A61B 6/032
378/62
4,150,293 A 4/1979 Franke
(Continued)

FOREIGN PATENT DOCUMENTS

WO 2014028930 A1 2/2014

OTHER PUBLICATIONS

International Search Report and Written Opinion corresponding to International Patent Application No. PCT/US2015/061679; dated Mar. 29, 2016; 14 pages.
(Continued)

*Primary Examiner* — Hoon Song
(74) *Attorney, Agent, or Firm* — Lathrop Gage LLP

(57) ABSTRACT

A CT scanner has multiple X-ray sources on a first rotatable gantry disposed to illuminate an X-ray detector array. An image processor receives data from the detector array, machine readable instructions in the memory include instructions for energizing K>=2 X-ray sources simultaneously while rotating the gantry through multiple positions and recording measurements at each gantry position. Some measurements correspond to sums of line integrals of radiation from two or more of the X-ray sources as attenuated by passage through an imaging zone to detector array cells, including a first measurement $N_{mp1}$ at a first gantry position and a second measurement $N_{mp2}$ at a second gantry position represent a sum of line integrals comprising a line integral of attenuation of radiation along a same line L. Instructions determine individual line integrals along the line L from the measurements $N_{mp1}$ and $N_{mp2}$ that include sums of line integrals along the line L.

29 Claims, 19 Drawing Sheets

Related U.S. Application Data

(60) Provisional application No. 62/117,868, filed on Feb. 18, 2015, provisional application No. 62/118,591, filed on Feb. 20, 2015, provisional application No. 62/186,991, filed on Jun. 30, 2015, provisional application No. 62/286,303, filed on Jan. 22, 2016.

(52) U.S. Cl.
CPC ............ *A61B 6/4452* (2013.01); *A61B 6/035* (2013.01); *A61B 6/54* (2013.01)

(56) References Cited

U.S. PATENT DOCUMENTS

| | | | |
|---|---|---|---|
| 5,841,141 A * | 11/1998 | Gullberg | G01T 1/1642 250/363.03 |
| 6,973,158 B2 | 12/2005 | Besson | |
| 8,755,493 B2 | 6/2014 | Travish et al. | |
| 2006/0233295 A1 | 10/2006 | Edic et al. | |
| 2008/0049891 A1 | 2/2008 | Yin et al. | |
| 2009/0101838 A1 | 4/2009 | Boyden et al. | |
| 2010/0135454 A1 | 6/2010 | Noo | |
| 2010/0322498 A1 | 12/2010 | Wieczorek et al. | |
| 2011/0188724 A1* | 8/2011 | Bruder | A61B 6/032 382/131 |
| 2013/0121553 A1 | 5/2013 | Thibault et al. | |
| 2013/0251097 A1 | 9/2013 | Zou | |
| 2014/0241489 A1 | 8/2014 | Zhang et al. | |
| 2015/0366522 A1 | 12/2015 | Besson | |

OTHER PUBLICATIONS

Besson, G. M.; New CT system architectures for high temporal resolution with applications to improved geometric dose efficiency and cardiac imaging; Medical Physics 42, 2668-2678 (May 2015).

Besson, G.M.; Old Ideas New Again: A System Concept for Fast CT Using Semi-Conventional Approaches; The third international conference on image formation in X-ray computed tomography; pp. 303-306.

Besson, G.M.; A new CT system architecture for high temporal resolution with applications to improved geometric dose efficiency and sparse sampling; Medical Imaging 2015: Physics of Medical Imaging, edited by Christoph Hoeschen, Despina Kontos, Proc. of SPIE vol. 9412; pp. 94120Y-1-94120Y-11.

* cited by examiner

MULTI-SOURCE CT SYSTEM AND IMAGING METHOD

CLAIM OF PRIORITY

The present document is a continuation in part of U.S. nonprovisional patent application Ser. No. 14/946,626 filed 19 Nov. 2015. This document also claims priority to U.S. Provisional Patent Application 62/117,868 filed 18 Feb. 2015. The present document also claims priority to U.S. Provisional Patent Application 62/118,591 filed 20 Feb. 2015. The present document also claims priority to U.S. Provisional Patent Application 62/186,991 filed 30 Jun. 2015. The present document also claims priority to U.S. Provisional Patent Application 62/286,303 filed 22 Jan. 2016. The contents of the aforementioned patent applications are incorporated herein by reference.

FIELD OF THE INVENTION

This disclosure relates to the field of electromagnetic (EM) radiation imaging systems, and more particularly to multi-source, simultaneous, radiation exposure in computed tomography (CT) imaging systems. In particular, the disclosure addresses methods, algorithms and systems for X-ray radiation CT imaging using simultaneous exposure from two or more radiation sources, although it is not limited to the imaging of radiation sources in the XX-ray energy range.

BACKGROUND

X-ray projection imaging or CT imaging provides a number of benefits, as is known in the art. CT requires acquiring projections or views from a multiplicity of angles around the object from which a tomographic image of structures within the object or patient is derived.

Since the beginning of CT, cardiac imaging has been a key technology driver. Multiple innovations have attempted to address the associated need for high temporal resolution. Although current CT systems can image a cross-section of the heart in about 100 milliseconds, this may not be sufficiently fast for full diagnostic information collection, and artifacts due to motion may still corrupt images reconstructed by today's machines.

Faster complete data acquisition sufficient for reconstruction of a tomographic image of a slice of interest are enabled through what is known in the art as "half-scan," or "partial-scan" imaging, where projections are acquired for a particular slice to be imaged during a gantry rotation angle less than 360 degrees.

CT systems with a rotating gantry typically have only one radiation source; although at least one medical imaging system is commercially available with two radiation sources.

In the available medical imaging dual-source CT system, the two X-ray tubes are offset by an angle of about 95 degrees. In this system, however, the second imaging chain with a radiation source and a detector does not cover the full imaging field of view: the corresponding projections are truncated. Also in that system the projections from the two sources do not overlap, so no cell in the detector sub-system is simultaneously irradiated by the primary beams from both sources.

Security imaging, such as aviation security imaging, also requires high scanning throughput, which is improved by high temporal resolution. Security CT systems with rotating gantries are available with two radiation sources: in one design, the two sources are positioned as close as possible and power is pinged from one to the other at various kVp levels, tube current, and beam filtration, to acquire dual-energy projection data.

X-ray sources are limited in the amount of power they can provide within a radiation frequency range useful for imaging of a human body or object. This power limit, as well as difficulties with rotating an-ray source at high angular speed, limit a CT imaging system temporal resolution.

SUMMARY

The systems and methods disclosed herein allow for high temporal resolution imaging and throughput in both medical imaging and security applications. In particular, CT system designs are disclosed that leverage a multiplicity of X-ray sources, a subset (possibly equal to the full set) of the source multiplicity being simultaneously active and generating X-ray projection beams, at least several of the active sources projections overlapping at least partially on at least a segment of the detector.

In an embodiment, a computed-tomography (CT) X-ray scanner has multiple X-ray sources mounted to a first rotatable gantry disposed to illuminate an X-ray detector array, the detector array having at least M detector cells. A support system for patients or objects to be inspected in an imaging zone lies between the X-ray sources and the X-ray detector array. A control and image processing system receives X-ray data from the X-ray detector array, the control and image processing system has at least one digital processor and a memory. Machine readable instructions in the memory include instructions configured to, when executed by the processor, energize an integer K of the X-ray sources simultaneously while rotating the first rotatable gantry through multiple positions and recording a measurements N at each gantry position P. Some measurements correspond to a sum of line integrals Lkmp of radiation from two or more of the K X-ray sources as attenuated by passage through the imaging zone to a cell of the detector array, the measurements designated Nmp; wherein a first measurement Nmp1 at a first gantry position P1 and a second measurement Nmp2 at a second gantry position P2, P1 and P2 being different, each measurement Nmp1 and Nmp2 representing a sum of line integrals comprising a line integral of attenuation of radiation along a same line L. Inversion machine readable instructions are configured to determine an individual line integral of attenuation along the line L from the measurements comprising ums of line integrals of attenuation along the line L.

In another embodiment, a method of performing computed-tomography (CT) X-ray scanning includes simultaneously generating X-ray radiation from a plurality of K X-ray sources, the X-ray sources being mounted to a first rotatable gantry; positioning the gantry at a position P1 and measuring X-rays received at M detector cells of an X-ray detector array disposed for illumination by the X-ray sources to generate multiple measurements N1; then rotating the first rotatable gantry to a second position P2 and recording a second multiple of measurements N2; where measurements N1 and N2 each corresponding to a sum of line integrals Lkmp of radiation from two or more of the K X-ray sources as attenuated by passage through an imaging zone to a cell of the detector array, and a first measurement Nmp1 in measurements N1 and a second measurement Nmp2 in measurements N2 represent a sum of line integrals comprising a line integral of attenuation of radiation along a same line L in both Nmp1 and Nmp2 sums. Then, the method includes determining an individual line integral of attenuation along the line L from the measurements comprising sums of line integrals of attenuation along the line L.

In yet another embodiment, a computed-tomography (CT) X-ray scanner has multiple X-ray sources mounted to a first rotatable gantry, wherein the X-ray sources are adapted for modulation. An X-ray detector array is disposed for illumination by the X-ray sources, the detector array having at least M detector cells, with an imaging zone between the X-ray sources and the X-ray detector array. A control and image processing system receives X-ray data from the X-ray detector array, the control and image processing system having at least one digital processor and a memory, and machine readable instructions in the memory. The machine readable instructions include instructions that, when executed by the at least one processor, energize an integer K of the X-ray sources simultaneously, while modulating the K radiation sources in known ways at known frequencies, and rotating the first rotatable gantry and recording a plurality of measurements $N_p$ at each gantry position P, at least a subset of the measurements corresponding to a sum of line integrals $L_{kmp}$ of radiation from two or more of the K X-ray sources as attenuated by passage through the imaging zone to a cell of the detector array, the measurements designated $N_{mp}$; wherein a first measurement $N_{mp1}$ at a first gantry position $P_1$ and a second measurement $N_{mp2}$ at a second gantry position $P_2$, $P_1$ and $P_2$ being different, each measurement $N_{mp1}$ and $N_{mp2}$ representing a sum of line integrals comprising a line integral of attenuation of radiation along a same line L, the measurements captured at a rate greater than a frequency of the modulation of the X-ray sources. The machine readable instructions also include inversion machine readable instructions configured to determine an individual line integral of attenuation along the line L from the measurements comprising sums of line integrals of attenuation along the line L, the inversion machine readable instructions constrained by the relative intensities of the known modulation of the radiation sources.

In another embodiment, a method of performing computed-tomography (CT) X-ray scanning includes simultaneously generating modulated X-ray radiation from K X-ray sources, the X-ray sources being mounted to a first rotatable gantry; positioning the gantry at a position P1 and measuring X-rays received at M detector cells of an X-ray detector array disposed for illumination by the X-ray sources to generate a plurality of measurements N1; rotating the first rotatable gantry to a second position P2 and recording a second plurality of measurements N2; where measurements N1 and N2 each correspond to a sum of line integrals $L_{kmp}$ of radiation from two or more of the K X-ray sources as attenuated by passage through an imaging zone to a cell of the detector array. A first measurement $N_{mp1}$ in measurements N1 and a second measurement $N_{mp2}$ in measurements N2 represent a sum of line integrals comprising a line integral of attenuation of radiation along a same line L in both $N_{mp1}$ and $N_{mp2}$; and determining an individual line integral of attenuation along the line L from the measurements including sums of line integrals of attenuation along the line L and known modulations of the K radiation sources.

In yet another embodiment, a computed-tomography (CT) X-ray scanner has multiple X-ray sources mounted to a first rotatable gantry, wherein the X-ray sources are adapted for beam-pinched gating; an X-ray detector array disposed for illumination by the X-ray sources, the detector array comprising at least M detector cells; apparatus for supporting a patient in an imaging zone between the X-ray sources and the X-ray detector array; and a control and image processing system coupled to receive X-ray data from the X-ray detector array, the control and image processing system having at least one digital processor and a memory, and machine readable instructions in the memory. The memory has machine readable instructions configured to, when executed by the at least one processor, alternately pulse an integer K of the beam-pinch gateable radiation sources, while rotating the first rotatable gantry and recording measurements $N_p$ at each gantry position P, at least a subset of the measurements corresponding to a sum of line integrals $L_{kmp}$ of radiation from two or more of the K X-ray sources as attenuated by passage through the imaging zone to a cell of the detector array, the measurements designated $N_{mp}$; wherein a first measurement $N_{mp1}$ at a first gantry position P1 and a second measurement $N_{mp2}$ at a second gantry position P2, each measurement Nmp1 and $N_{mp2}$ represents a sum of line integrals including a line integral of attenuation of radiation along a same line L. Inversion machine readable instructions are provided to determine an individual line integral of attenuation along the line L from the measurements comprising sums of line integrals of attenuation along the line L, the inversion machine readable instructions constrained by known pulsing of the radiation sources.

In another embodiment, a method of performing computed-tomography (CT) X-ray scanning includes simultaneously generating known pulses of X-ray radiation from a plurality of K beam-pinch gateable X-ray sources, the X-ray sources being mounted to a first rotatable gantry; positioning the gantry at a position P1 and measuring X-rays received at M detector cells of an X-ray detector array disposed for illumination by the X-ray sources to generate a plurality of measurements N1; rotating the first rotatable gantry to a second position P2 and recording a second plurality of measurements N2; where measurements N1 and N2 each corresponding to a sum of line integrals Lkmp of radiation from two or more of the K X-ray sources as attenuated by passage through an imaging zone to a cell of the detector array, and wherein a first measurement $N_{mp1}$ in measurements N1 and a second measurement $N_{mp2}$ in measurements N2 represent a sum of line integrals comprising a line integral of attenuation of radiation along a same line L in the sums represented by both $N_{mp1}$ and $N_{mp2}$; and determining an individual line integral of attenuation along the line L from the measurements comprising sums of line integrals of attenuation along the line L and known pulses of X-ray radiation from the K radiation sources. In a particular embodiment, the X-ray detector array is mounted on a second rotatable gantry.

DEFINITIONS

Figure 1:
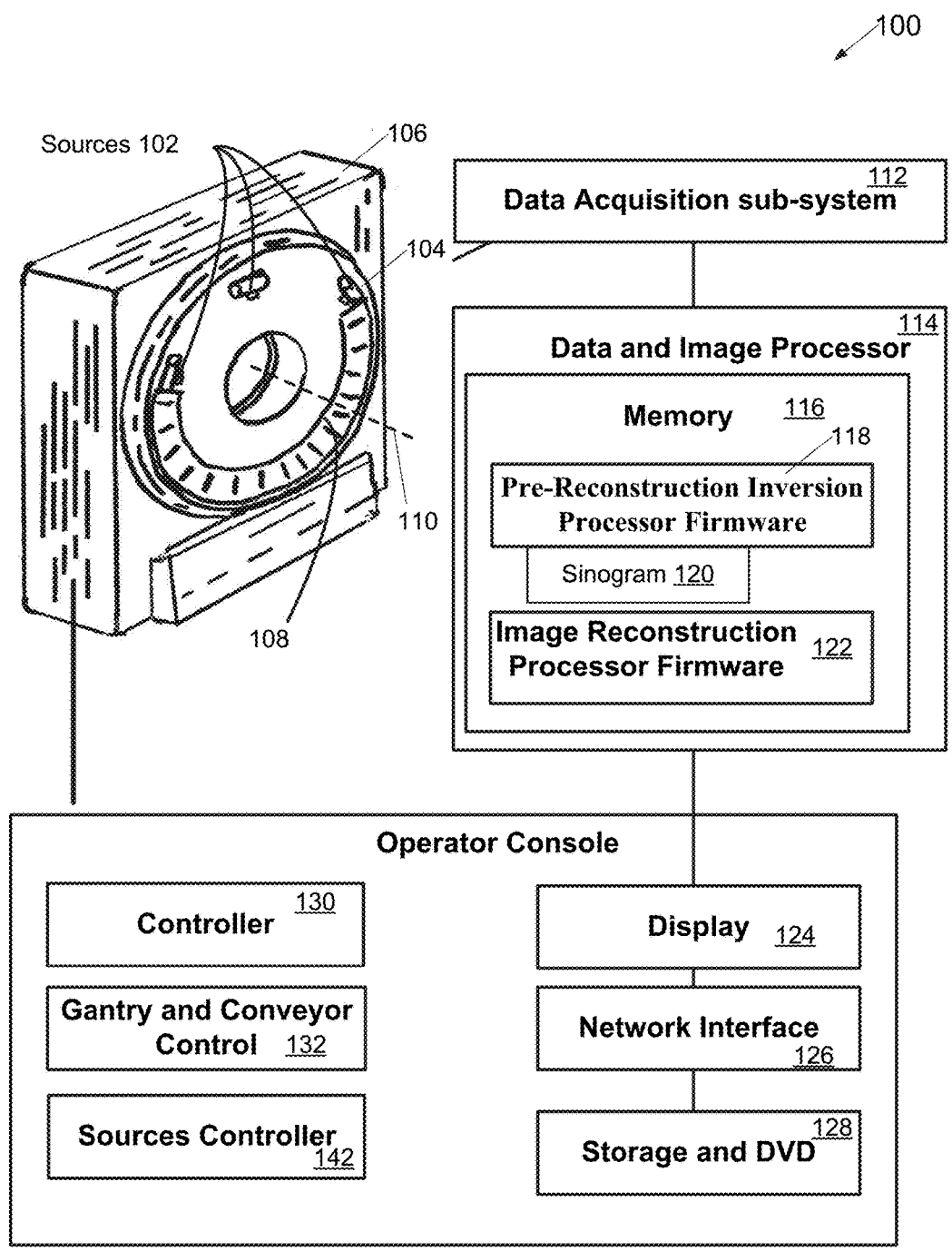
FIG. 1 is a diagram illustrating a CT system frame and gantry per an embodiment of the present invention.

The following terms are used in this invention disclosure with the specific meaning now described.

"Radiation source:" A punctual, individual source of radiation useful for imaging in CT. In particular, an X-ray source; this includes X-ray sources in all their variations, from individual X-ray tube, including fixed-anode tubes, rotating-anode tubes, to individual radiation source elements in a controllable array of radiation sources, to large radiation sources that sweep an electron beam in a vacuum envelope to define in time a spatial excursion of a radiation focal-spot (the area from which most of the useful radiation in the beam is emitted).

"Fan-angle:" the angle of a projection line from the source (modeled as a point source) to the center of one cell on an array of detector cells. Generally the fan-angle is measured from the central line joining the source to the system isocenter O. Thus an X-ray path or projection line fan-angle is relative to the source. However, in fourth-generation CT, the fan-angle is defined for a detector cell.

"Imaging or measurement field-of-view (MFOV) of radius $R_M$:" the radius of a disk centered on system isocenter O such that in normal operation the full field-of-view is exposed by one or a plurality of radiation source(s) for the acquisition of a fan-beam projection. The radius $R_M$ in turn is given by the measurement cell that is furthest away from isocenter, in third-generation CT geometry; in fourth-generation geometry, it is determined by either the X-ray source collimator(s) lateral extents or by the timing of individual detector cell data acquisition.

"Maximum fan-angle:" For a given distance $R_S$ from the isocenter O to a given source, the maximum fan-angle associated with the measurement field-of-view of radius $R_M$ is given by:

$$\Gamma = a\sin\frac{R_M}{R_S}.$$

In a fourth-generation geometry, the source radius distance $R_S$ is replaced by the detector radius distance $R_d$ in the equation above, since projection fan-beams are formed with a given detector cell as the fan vertex.

An "axial" scan occurs when the source rotates around the patient with the patient table not advancing through the gantry. Such a scan may include data acquisition over more or less than one 360-degree source rotation, as further explained below.

A "helical scan" occurs when the patient table is advanced through the gantry concurrent with X-ray source activation and rotation around the patient table.

"Full-scan:" Refers to a data acquisition mode wherein an X-ray source rotates 360-degrees around the patient or object to be imaged, and projection data for one particular slice in the patient are acquired over 360-degrees of view angles. In helical acquisition mode, the X-ray source rotates continuously within the gantry for an extended period of time (often termed "a scan"), and data for several "full-scans" are acquired in "a scan." Thus the term "scan" by itself can be ambiguous.

"Half-scan:" Refers to a data acquisition mode where for a given slice through the object, the X-ray source rotates and data are acquired over a source angle excursion equal to $\pi+2\Gamma$.

"Partial-scan:" Refers to a data acquisition mode where for a given slice through the object, the X-ray source rotates and data are acquired over a source angle excursion in the range $[\pi+2\Gamma, 2\pi]$. This is an extension of the concept of half-scan data acquisition described above.

All the above data acquisition modes may occur during a scan comprising source exposure and data acquisition from a multiplicity of rotations. In that case, the respective terms apply to the reconstruction of a specific image surface from a subset of the total "scan" projection data.

"Central angle:" The angle between two lines passing through isocenter O, and measured at O. It is convenient to specify source angles, source separations, and detector angular extents, in terms of their respective central angles. If there is potential ambiguity regarding angles between lines in three-dimensional space, such as is the case when sources are offset along the rotation axis z from one-another, then the term central angle in this document refers to the angle between the lines as projected onto the main gantry plane x-y orthogonal to the rotation axis z.

"System matrix:" By linearization of the CT data acquisition problem it is possible to represent the relationship between the unknowns (object/image pixel linear X-ray attenuation coefficient values) and the measurements (projection measurements acquired by the detector) by a matrix, termed the "system matrix."

"Inverse Problem:" A problem involving the estimation of unknowns from a set of measurement, most measurements relating two or more unknown in a single equation. The inverse problem may be linear or not.

"Matrix Inversion:" The algebraic process of determining unknowns from a set of measurements in a linear formulation of a problem.

"Under-determined inverse problem:" An inverse problem with more unknowns than measurements.

"μl-posed inverse problem:" An inverse problem such that noise or uncertainties in the measurements are amplified through any attempt at inversion. The system matrix for such an imaging system, either as posed or as a result of linearization, then exhibits a large "condition number," as is known in the art. Computed tomography is a proto-typical example of a data acquisition modality leading to an ill-posed inversion problem, that of reconstructing tomographic images from the acquired projection data.

"Regularization:" An under-determined or ill-posed inverse problem can be regularized by the use of a-priori information about the object being imaged. That is, specific constraints are applied to the problem. For example, in CT imaging, we know the unknowns (which are the linear attenuation coefficients of the object being imaged) to be positive. Thus we can require our inversion estimates to be positive.

"Primary beam:" The fraction of an X-ray beam transmitted through an object without deflection or scattering.

"Scattered radiation:" any X-ray radiation that has undergone a deflection/scattering event with respect to its originally straight travel path.

"Simultaneous exposure:" In the context of this disclosure, simultaneous exposure occurs when two or more X-ray/radiation sources are simultaneously active and irradiating the patient/object to be imaged.

"Simultaneous exposure of an individual detector cell:" In this document, simultaneous exposure of an individual detector cell occurs when two or more X-ray sources are simultaneously active and their projections overlap on at least part of the detector; that is, at least one detector cell is being impinged by primary beams from two or more X-ray sources. In the following the term "simultaneous exposure" is also used with this meaning when there is no risk of confusion.

"Radiation source array:" A plurality of individual X-ray sources provided as a single sub-system. In specific cases, the individual X-ray source elements within the array can be addressed or controlled individually.

"Activated (pertains to a radiation source):" The radiation source is energized and is ready to produce a radiation beam. For example, in a conventional X-ray tube, the filament may be heated by a current and electrons "boiled off." However, the electron beam to the anode may be cut-off or pinched by an applied voltage, so that the amount of emitted radiation is either non-existent or very small. So an activated radiation source may emit a radiation beam or not.

"Detector," also "radiation detector:" Refers to the sub-system comprising the entirely of radiation measurement cells; each of these cells gives rise to a measurement at specific time intervals ("time sampling intervals") and is referred to as an "individual detector cell." Detector cells may be arranged on a variety of surface configurations; all the cells in a detector do not need to form a contiguous surface. A detector may include several components, such as separate detector arrays. For illustration, in some configurations, a component of the detector is rotating on a gantry, and another component of the detector is fixed in the laboratory coordinate system. In photon counting detectors, a cell generates a signal each time an X-ray interacts within the cell. In this document, it is understood that the detector array may have several rows, generally the rows being offset from one-another in the direction of the system rotation axis z. In the document, it is referred to a "detector arc," meaning the curve that represents the trace of the detector surface as it intersects the main gantry plane x-y. The detector arc, as any curve in three-dimensional space, may have a curvature center. The curvature center may vary locally along the arc, as is the case when the arc is not an arc of a circle.

"Central ray:" A mathematical line from the mathematical, punctual center of source to the detector passing through the system isocenter O.

"Gantry:" Mechanical apparatus supporting a rotating source, array of sources, or plurality of sources, and optionally one or a plurality of detector(s).

"Drum:" Part of a gantry, a drum is a mechanical device that rotates around the patient or object to be imaged in CT. Thus a CT system may present one or more rotating gantry/drums. Synonym for "rotating gantry" component.

"Image reconstruction:" The CT inverse problem of recovering the object linear attenuation coefficient spatial distribution from a set of projection measurements. It is understood that, although the process of image reconstruction typically yields one two-dimensional cross-sectional image of the object, it in fact performs a three-dimensional attenuation map reconstruction, since the process of two-dimensional reconstruction starts by selecting a plane or surface of interest within the three-dimensional object, then continues by selecting projection data associated with this surface ("sinogram") and then performs the tomographic reconstruction itself. Further, successive tomographic slices are typically processed in sequence. In the sense that the data for a given slice is associated to a particular time interval, the CT reconstruction in effect reconstruct a slice of a four-dimensional volume (where one reconstructed three-dimensional volume corresponds to a "snapshot" of the living body in a given time interval). The three-dimensional reconstructed image, or attenuation map, is represented on a set of volume elements, or voxels.

"Projection:" A set of measurements normally associated with a source at a given position with respect to the object. In CT, a given projection is considered complete if substantially all mathematical lines from the source through the measurement field-of-view are substantially traversed by an X-ray beam and give rise of a detector measurement. Also called a "view." The term projection is also used to denote the mathematical set of lines originating at a source, passing through the MFOV, and impinging on the detector; whether or not actual radiation beams are emitted by the source.

"Fan-beam projection:" In CT, projections are acquired at a given time in the form of a fan of rays emitted by a source, irradiating the measurement-field-of-view, and then impinging on a detector. In any practical implementation, a fan-projection is acquired during a finite time interval, called the "detector integration time."

"Projection ray:" Geometrically, a line from a punctual radiation source to the punctual center of an individual detector cell at a given time.

By extension, a projection ray: the geometric envelope of the lines originating from one point on the X-ray source focal spot and ending on the surface of an individual detector cell at a given instant in time. Thus a projection ray in this sense is a beam around a center line with a limited three-dimensional spatial extent and a cross-section area in a plane orthogonal to the projection ray above defined. Thus a ray corresponds to the envelope of the X-ray paths extending from the entire active focal spot area on the X-ray source to the entire active detector cell area, at a given instant in time. To each ray through the object we associate a line-integral of the object linear attenuation coefficients.

By extension, a projection ray: corresponds to the total three-dimensional volume obtained when the three-dimensional beam described above corresponding to one instant in time is swept during an integration time corresponding to the acquisition of one detector cell sample. To such a projection ray, we associate a line-integral and a measurement at the detector.

"Line-integral:" The measurement associated to a projection ray in a CT system. A projection typically comprises several hundred line integrals; and a complete data set (see "sinogram") for one image to be reconstructed typically comprises several hundreds of projections worth of line-integral data. The line-integrals form the input to the image reconstruction methods/process—independently of the specific of the image reconstruction algorithm; that is, all reconstruction algorithms take as input the line-integral data, also referred as the "individual line-integral" data, as opposed to the summed projection data that are part of the present invention. A line-integral L refers to an integral of attenuation over a path; and the description below by abuse of language occasionally use the term line-integral to refer to a geometric path through the object, or a line associated with this path, corresponding to the individual line-integral measurement.

"Detector quarter-offset:" A system configuration whereby by offsetting the detector such that a central ray from a source intersect a detector cell at ¼ or ¾ of its width, the conjugate ray of a given line-integral L—acquired after substantially 180-degrees gantry rotation—will be sampled that is parallel and laterally offset from L by about ½ of the detector width. This enables the acquisition of sinogram data sets with higher spatial resolution. Conversely, the quarter offset can be ignored and the conjugate ray considered to provide a second estimate of line-integral L. Similar sampling effects are achieved by deflecting the electron beam focal spot on the X-ray target, either magnetically or electrostatically.

"Summed projection data," or "summed line-integrals:" In the CT systems described herein, some line-integrals may be measured individually; but most line-integrals are measured in sums; that is, a given measurement is associated to radiation detected along a plurality of paths originating from several radiation sources and ending on one detector cell at a given time/time-interval. It is thus necessary to examine conditions under which the individual line-integral data may be estimated from the summed data, as is required for image reconstruction. This disclosure describes CT systems that lead to summed data from which the individual line-integral estimates may be recovered, and methods of doing so. This implies necessarily solving an inverse problem.

Thus the systems and methods of the present invention are concerned, at least in part, with the setting and solving of a "pre-reconstruction inverse problem." As is described in the disclosure, specific CT system designs lead to conditions that are favorable to the solving of this problem. The pre-reconstruction inversion problem works with the summed measurements as inputs and provides as output estimates for the individual line-integral measurements that are the inputs to the CT image reconstruction process. In particular, in this document two types of situations are outlined: "local pre-reconstruction inverse problem" and "global pre-reconstruction inverse problem." By local it is meant that individual-line integral estimates can be obtained by solving, for each line-integral L, a system with K or fewer rows, where K is the number of sources simultaneously in view of the detector. By contrast, a global inversion is one that operates on substantially all of the sinogram data set associated with one image to be reconstructed.

"Line-integral bundle," or "L-bundle:" In the CT systems of the present invention, often measurements of one specific line-integral involve other line integrals, through the summed projection data described above. In specific embodiments, for a system having $N_S$ radiation sources, over a half system rotation, $N_S$ summed measurement will involve a particular line-integral L. To each such measurement is associated a set of up to $N_S-1$ other individual line-integrals. Thus the set of all individual line-integrals associated through summed measurement with line L is described as the "L-line-integral bundle," or line-integral bundle for short. Since each individual line integral is associated to an unknown, the L-bundle corresponds to a set of unknowns that can be retrieved through a pre-reconstruction inversion process. To each L-bundle is associated a corresponding set of equations, the solution of which provides estimates for each of the individual line-integrals associated with the summed measurements for the L-bundle.

A projection is "truncated" if some rays in the projection that intersect the imaging field-of-view do not lead to a measurement; this does not include the effect of X-rays falling on an anti-scatter grid element or septa separating two cells on the detector.

Conversely, a projection is "un-truncated" if all projection rays intersecting the imaging field-of-view lead to a measurement.

Sinogram (single row and multi-row detectors):" A sinogram is a set of projection data associated with a given slice through the object. The sinogram is thus the data set used by a given CT image reconstruction algorithm to generate a tomographic image in a pre-selected slice of interest. In CT, it is often arranged as a set of views, each including a set of detector cell measurements. A typical CT sinogram contains about 1,000 views or projections, each projection containing several hundred measurements. During a typical scan, projection are acquired that can be re-arranged/re-organized into sinograms in a number of ways. We associate the term sinogram to the set of data that will be used for the reconstruction of a specific tomographic image.

"Detector distance:" In this document, the term "detector distance" means the smallest (minimum) of the distances from the system isocenter O to the detector surface along the central rays from the various sources to the detector surface.

"Flying detector:" In this document, a "flying detector" is a detector mounted on the inside surface of a rotating gantry; the rotating gantry being generally cylindrical in shape and centered on the system isocenter O. In operation, the flying detector rotates inside a second gantry that supports a plurality of radiation sources. The flying detector comprises an extended aperture of dimensions such that X-ray sources arranged on the gantry external to the flying detector can illuminate therethrough over a central angle substantially equal to $(\pi-2\Gamma)$ radians; therefore, depending on the geometry of the system, and the dimensions of the outer gantry supporting the sources, the actual aperture dimension may differ to some extent from the nominal $(\pi-2\Gamma)$ radians; this aperture is referred to as the "extended flying detector aperture" or "extended aperture" for short. The outer gantry, supporting the X-ray sources, may be either rotating or fixed in the laboratory reference frame (if it rotates, it can rotate in either direction with respect to the flying detector rotation direction). The flying detector has active detector cells distributed over a central angle substantially equal to the complementary central arc in $2\pi$ radians, that is $(\pi+2\Gamma)$ radians. The flying detector may have one or a plurality of detector cell rows, generally arranged along the z direction. It may have other elements as known in the art, including anti-scatter-grids (ASGs); the ASGs lamellas may be arranged in a direction generally parallel to the central imaging plane defined by axes x and y. The flying detector may include indirect or direct radiation detection elements as known in the art. Also called "flying detector gantry."

A radiation source is said to be "in view of the detector" or "visible from the detector" if it is activated, and such that when the source is not muted (as by electron-beam pinching as described above) some of the fan-beam of radiation originating from the source, exiting the source collimator, and intersecting the imaging field-of-view, impinges or would impinge on the surface of radiation detector (whether on a radiation detection element, an ASG lamella, or another component of the radiation detector). That is, the corresponding projection is un-truncated. In the context of a system with a flying detector, this implies that rays from such a source passing through the MFOV is not blocked by flying detector components other than the entrance surface of the radiation detector; i.e. during the (short) time duration that a subset of the mathematical lines from the source through the MFOV are blocked by the flying detector, the source is NOT considered in view of the detector.

"Source distance:" In general, the radiation sources will be positioned on a gantry, either rotating or fixed, at substantially the same distance from isocenter. However, in specific designs, this distance may vary from source to source; in particular, should radiation source arrays be generally arranged on flat surfaces, then the distances from the various individual source elements to O (or to the rotation axis) will vary slightly. More generally, it may be desirable to position the sources at position offsets with respect to their distance to O. In the claims, the term "source distance" and the variable $R_S$ means the smallest (minimum) of the distances from the system isocenter O to the radiation sources focal spot centers along the central rays from O to the respective radiation source focal spot centers.

"System fan-angle ($\Gamma$):" Similarly, since the maximum useful fan-angle is generally associated to the radius of the measurement/imaging field-of-view $R_M$ and to the source distance, to each source corresponds a maximum fan-angle value $\Gamma$ as previously described. In this document, by system fan-angle or Greek letter $\Gamma$ it is meant the largest of these fan-angles, associated with the one source the closest from isocenter; in other word, is defined by $R_M$ and the source distance $R_S$ defined above; Thus the system fan-angle is given by:

$$\Gamma = \text{asin}\left(\frac{R_M}{R_S}\right).$$

Naturally in a fourth-generation-like architecture, the definition is:

$$\Gamma = \text{asin}\left(\frac{R_M}{R_d}\right).$$

"Extreme sources:" $\theta_S$ is the central angle between the two extreme sources in a set of $N_S$ sources arranged over a central angle generally less than $(\pi-2\Gamma)$ radians on a rotating gantry, whether the sources be equispaced or not. In a system with a flying detector, and either a rotating source gantry of a fixed gantry supporting a large number of sources, the extreme source angle $\theta_S$ represents the central angle between the two extreme sources in view of the detector at a given time t through the flying detector extended aperture. Thus in principle, the extreme source angle can vary with time, $\theta_S=\theta_S(t)$. In a preferred embodiment, the sources are equi-distributed in central angle over a central angle less or equal to $(\pi-2\Gamma)$ radians. In general, a dual-drum CT system will have $N_S$ sources, a subset of K sources at a given time being in view of the detector and defining a central angle $\theta_S=\theta_S(t)$.

When the sources are equispaced, the angle $\Delta\theta_S$ represents the central angle between two adjacent sources.

A set of $N_S$ radiation sources is said to be "partially overlapping" if the projections associated with adjacent sources, virtual or actual radiation projections, overlap at least partially on at least part of the detector. Thus when radiation sources are partially overlapping, at least a subset of the detector cells would give rise to summed line-integral measurement(s), when X-ray beams are emitted by the adjacent sources.

A CT system isocenter is a location, generally coinciding with the system center of rotation in the gantry central plane. It is understood that due to mechanical tolerances, vibrations, the system isocenter in practice lies within a small, mathematically defined, volume of space. It is generally located on the system rotation axis, see below.

"System rotation axis" or "rotation axis:" Generally defined as the z axis; is the axis of rotation for gantries carrying the radiation sources, the radiation detector, or both. This is an imaginary line associated with the main rotational movement of the gantry, and generally perpendicular to the main imaging plane; the main imaging plane itself containing two mathematical coordinate axes for x and y. The intersection of the rotation axis and the main imaging plane defines the system isocenter O, c.f. above description, a mathematical point from which various system distances are measured. In case of elements being offset in z from the system central planes, their respective distances "from isocenter" are in fact measured from the system axis of rotation. Thus their "distances" refer to distances to/from the rotation axis.

"Source modulation:" By source modulation in this document it is meant spectral modulation, as well as modulation of other source parameters, such as focal spot size, polarization, and other relevant parameters. Specifically with respect to spectral source modulation, it is meant any change in the function defining the radiation amplitude distribution at each frequency; including the definition of the spectral function support—that is that range of frequencies where the radiation source output cannot be considered so small as to be negligible.

In this document, the terms "asin" or "asine" refer to an Arcsine function, an inverse of sine function. More specifically it refers to the inverse of the sine function with range −90 degrees to 90 degrees.

The description below assumes clockwise system rotation; actual system rotation can be in either direction. In particular, when relevant, the source drum and detector drum can rotate in opposite directions; as well as in the same direction (in different scans performed by a system).

The System

Before proceeding with the detailed description, it should be noted that the matter contained in the following description and/or shown in the accompanying drawings may be embodied in various forms, and should therefore be interpreted as illustrative, and not in a limiting sense. Elements shown in the drawings are not necessarily to scale and may be exaggerated, enlarged or simplified, to facilitate understanding of the invention.

The invention applies to various CT and projection imaging configurations. For illustration, in the CT case, the invention applies in particular to "third-generation" CT geometry, wherein two or more sources are mounted on a rotating gantry, with a detector array arranged generally on a surface intersecting the main gantry plane on a line or arc opposite the source with respect to the patient or object to be imaged. The invention also applies to various other CT imaging geometries, such as a set of X-ray sources facing a flat-panel detector array, or other type of detector array, or a set of X-ray sources facing a narrow-aperture configuration detector array, that is an array that is rectangular and in some applications meant to be scanned in a direction generally at an angle with respect to its long dimension. The X-ray sources may be offset in various directions from one-another.

The invention also applies to an array or arrays of sources, such as arrays of individually addressable X-ray sources (whether in a rectilinear or matrix format) arranged on the surface of a plane or on a curved surface.

In an imaging situation, it is desirable for the radiation source(s) to have the attributes described below. The ideal form of these attributes is considered unachievable; however it is an aim of scientific and technological advances to approximate those conditions as closely as possible. Since X-ray imaging works in projection, the spatial resolution of the observed image is uniquely defined by the paths from the source focal spot or surface area to the various detector elements. It is thus desirable that the X-ray source be a point-source, or at least of as small as possible a spatial extent as practical; source blurring (made worse in specific geometries by magnification) typically contributes a limiting factor to the overall system resolution performance.

Further, ideally the X-ray source should have as high power as possible. At least three factors lead to this requirement. First, and as mentioned above, it is desirable for the source area to be as small as possible, therefore leading to high power per given area. Second, temporal resolution requirements lead to the use of a short exposure time—typically to avoid or reduce effects due to contrast, patient or organ motion during an exposure. Third, X-ray radiation is broad-band in nature, but optimally a specific X-ray energy (or narrow energy band) could be specified as a function of object attenuation in the beam path; while tuning the source to that specific frequency, or at least to a narrow frequency band containing the desired frequency, is currently not achievable commercially with practical sources, it is possible to filter the beam to at least remove a significant part of the radiation below that specific frequency or frequency band. However, filtering also reduces the beam output within the desired frequency band.

In X-ray imaging, useful radiation—radiation such that the object to be imaged is semi-transparent to it—is typically obtained by bombarding with high energy electrons a target material in an anode. High Z materials are preferred as they provide more intense radiation. The resulting broad-band frequency radiation, "bremsstrahlung" or "braking radiation," typically contributes the largest radiation energy out of the target, although specific materials such as Rhenium (Rh) and Molybdenum (Mo) have marked K-edge radiation peaks corresponding to K-shell atomic transitions. By far, the material the most commonly used for anode targets in X-ray medical imaging and security or inspection imaging is Tungsten (W).

The spectra obtained as a result of target electronic bombardment has a maximum emission energy defined by the maximum energy of the impinging electrons, which in turn is set by the peak-kilo-voltage (kVp) applied to the tube or source. The lowest energies are a function of a tube self-filtration resulting from, in part, the material used to define a functional tube vacuum envelope; typically glass or metal. In medical imaging, it is common practice to provide an additional layer of filtration immediately in front of the source (on the X-ray paths toward the patient and then the detector) to eliminate or at least significantly reduce the intensity of low-energy X-rays. This is done because those low energy X-rays have low penetration power and in most applications contribute primarily to the patient dose (such as in skin dose), but very little to observed signal. X-ray attenuation of a thin monochromatic (energy E=hv where h is Planck's constant and v the frequency of the emitted monochromatic radiation) pencil beam through a (thin) slab of thickness L and attenuation $\mu(E)$ follows Beer's law of attenuation:

$$I(E,L,\mu)=I_0(E)\exp(-\mu(E)\times L),$$

where $I_0$ is the intensity that would be measured without any object or patient in the beam, or intensity of the object impinging beam along the specific pencil-path, and I is the exiting beam intensity (at single energy E). So $I_0$ in this equation refers to the energy that a detector would measure in the absence of any object in the beam path.

Throughout this document, it is understood that various sources among a system's multiplicity of radiation sources may emit radiations of various spectral properties and with various focal spot intensity distributions. The various spectral properties come from, as is known in the art in the case of X-ray sources, choices of target material, tube current (mA), peak kilo-voltage (kVp), and beam filtration. The focal spot intensity distribution varies depending on the beam optics properties of each source. Thus, for example, a subset of the system sources may be operated at a given kVp, beam current, and beam filtration, and a second subset at another kVp, beam current, and beam filtration. Many combinations are possible.

Up-to-now, simultaneous exposure of the same detector cell, or set of detector cells, by multiple radiation sources, has been generally avoided in scientific, commercial and medical EM applications that rely on transmission imaging through a semi-opaque medium and direct image formation (without an optics forming element such as a pin-hole, lens, or combination thereof). In such a setting it is a-priori difficult or impossible to separate the signals due to the respective sources since in the absence of a lens, the imaging geometry is uniquely specified by the lines joining the sources and a given detector cell; the radiation from one source typically reaches the entirety of the useful detector array; indeed under "ideal imaging conditions" the exposure intensity from one source (without intervening object) would be uniform across the useful detector array. Accordingly, simultaneous exposure of an object onto a common set of detector cells leads to commingling of the detector signals where the X-ray projections from the two or more sources overlap; with no a-priori means to separate the summed projection signal into the various constituents that are to be associated with each of the simultaneously active sources. Thus, simultaneous exposure with projection overlap is not applied in current state-of-the-art X-ray or CT imaging.

As a result, in a setting where multiple radiation sources are "in view" of the detector, and where it may be desirable to leverage the multiple sources—for instance for flux or power reasons, a multiplexing approach that relies on temporal, spectral multiplexing, or an approach combining several of these elements is considered.

Multiplexing the sources, however, typically restricts the maximum flux available from the respective sources: Temporal multiplexing pulses the sources and limits emission of a given source to the time period when that source is turned on. Spectral multiplexing limits a given source output to a given energy band, either intrinsically within the source or by external radiation filtration. In either case, the total source output is considerably reduced, and thus the main impetus for having two or more sources simultaneously in view of the detector is not met.

In CT, temporal resolution gains are achieved by increasing the source rotation speed around the object. However, this imposes source output power requirements that are difficult to achieve, since the X-ray source output must increase in direct proportion to the source rotation speed increase to maintain a given level of X-ray flux, and thus signal-to-noise ratio, per view/projection and per tomographic slice to be reconstructed. Novel CT system architectures are proposed that relies on the simultaneous exposure of at least part of a detector array to break through the flux limitation and achieve higher temporal resolution (G. M Besson, Medical Physics 42, 2668 (2015); doi: 10.1118/1.4918328).

In all X-ray applications, including projection imaging and CT, it would be desirable as described above to have access to sources of arbitrary power. Since any individual source is necessarily limited, it is desirable to leverage several sources and their combined power under simultaneous exposure conditions. This could range in principle from the use of two sources to implementations with arrays comprising a large number of individually addressable sources.

Arrays of individual X-ray source emitters are now becoming possible, and some such technologies are in the prototype stage. XinRay Systems (7020 Kit Creek Rd #210, Durham, N.C. 27560) has developed linear arrays of individually addressable sources (http://xinraysystems.com/), utilizing proprietary carbon nanotube based X-ray sources. U.S. Pat. No. 8,755,493 discloses piezoelectric or pyroelectric crystals capable of generating high-energy electron beams and thus X-rays; the technology is potentially available to form an array of point sources. Tribogenics (5440 McConnell Ave, Los Angeles, Calif. 90066; http://tribogenics.com/) has developed an alternative way to emit high-energy electrons that may also in specific implementation be amenable to the design of arrays of X-ray sources.

Moving or rotating the source around the patient as required in CT imaging with a single source, also limits achievable temporal resolution for mechanical design reasons. High-power conventional X-ray sources currently in CT systems implement a rotating anode approach; the rotating anode being placed in vacuum envelope, or tube, which itself rotates in the gantry around the patient or object to be imaged. Large power requirements lead to large anodes and tube sub-systems, and high angular velocity gantry rotations places significant mechanical strain on all rotating components.

In alternative embodiments, two or more X-ray sources, or arrays of sources, are mounted on a gantry; the gantry moving with respect to the patient. Use of multiple sources reduces the range of mechanical excursion required for a complete data acquisition for any tomographic slice or set of tomographic slices to be reconstructed; in the case of array(s) of sources, it may even alleviate the motion requirement in part or completely. These approaches thus potentially help improve temporal resolution. Also, they provide practical ways to perform multispectral imaging of an object; for example by allocating sub-sets of sources to each spectrum to be used in the multispectral data acquisition.

Thus, simultaneously irradiating the patient or object to be imaged by two or more X-ray sources is desirable. Further, it is desirable to obtain this capability while active source projections overlap on the detector; otherwise, simple geometric considerations limit to about three the maximum number of sources that are simultaneously active without projection overlap in a typical medical CT geometry.

The disclosure presents a general method or algorithm to recover the individual line integral projection data from combined (summed) data obtained with simultaneous radiation exposure, in the general case of a CT system comprising K simultaneously active radiation sources and performing a complete or partial ("half-scan" or "partial-scan") revolution around the patient or object to be imaged.

In the general situation where a CT system comprises K simultaneously active sources specific methods are presented to regularize the pre-reconstruction inversion and recovery problem. These imaging methods rely on the use of radiation source modulation in time to encode information associated with each one of K simultaneously active radiation sources; the projection data associated with each individual source is then recovered through correlation analysis of the summed projection data; or using correlation as an a-priori constraint on the recovery problem.

Further, an imaging method for regularization of the pre-reconstruction inverse problem is disclosed to facilitate recovery of individual line integral data associated with each individually labeled source from a summed measurement; the method relying of the acquisition of individual source data for sampling time sub-intervals, and thus providing additional a-priori information for the regularized inversion of the problem.

A multiple-source CT scanner system 100 (FIG. 1) as described herein has multiple radiation sources 102, which in a particular embodiment are X-ray tubes. The radiation sources 102 are mounted in a generally cylindrical, rotatable, gantry 104 rotatably mounted in a frame 106. Rotatable gantry 104 has a cylindrical passage in which a patient or object to be scanned is positioned on a movable table or conveyor (not shown) that passes through the passage. The cylindrical passage has an axis 110 the intersection of which with the main plane of the gantry is known herein as the isocenter of the system. Axis 110 coincides with the gantry(ies) rotation axis. A radiation detector array 108 is mounted to receive radiation emitted by sources 102 that may have passed through the patient or object in the passage. In some embodiments the detector array 108 is mounted to the source gantry and rotates with the tubes, in other embodiments the detector array is mounted to the frame, as described herein; in some embodiments as described herein the sources and the detector are mounted on separately rotatable gantries. Detector array 108 is coupled to provide radiation detection measurements through a data acquisition subsystem 112 into a processor 114. Processor 114 has a memory system 116 that contains an inversion firmware 118 that processes detector data into a sinogram 120 through the pre-reconstruction inversion process described therein. Memory 116 also contains an image reconstruction firmware 122 that constructs tomographic images of the patient or object to be scanned; the tomographic images may be viewed on display 124, uploaded via network interface 126 into an electronic medical records system (not shown) or radiological database, or written onto DVD's for physical record storage, radiologist review, or transfer to other facilities. Gantry(ies) 104, radiation sources 102, and data acquisition 112 all operate under control of a controller 130 and gantry & conveyor control 132. Controller 130 also contains specific firmware 142 for the control of the various radiation sources parameters during a scan.

Figure 2:
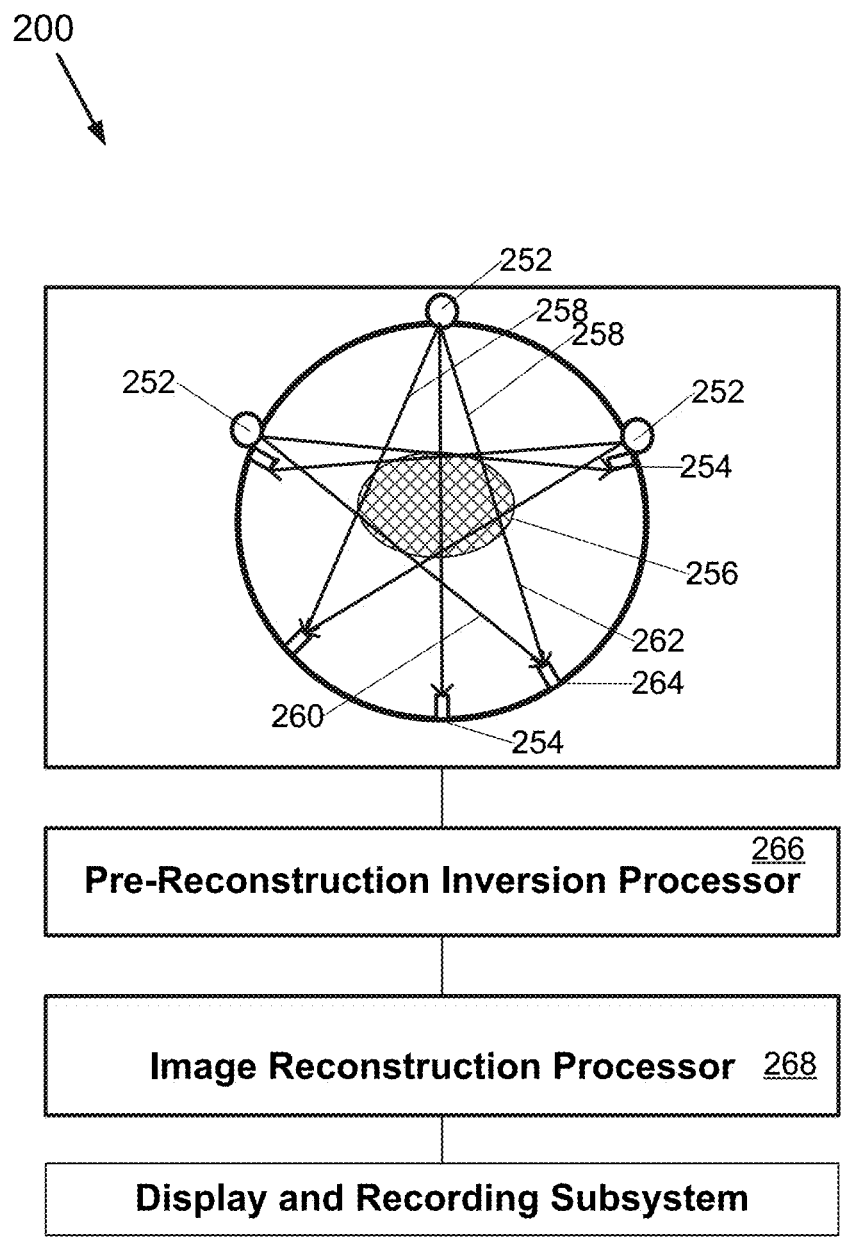
FIG. 2 is a schematic representation of the CT system of FIG. 1.

System 100 is representable schematically as illustrated in FIG. 2, 200, where radiation sources 252 are represented as circles and specific individual detector elements 254 of the radiation detector array are represented as rectangles. In a typical embodiment the radiation detector presents a substantially continuous surface to impinging radiation in such a manner that direct lines from the source(s) through the patient intersect it: The patient or object to be scanned 256 is located such that at least some lines 258, 260, and 262 drawn from radiation sources 252 to radiation detector elements 254, 264 pass through the patient or object 256. When radiation sources 252 are active, X-ray radiation passes along each line 258 to the detector elements, and some of the radiation is absorbed by patient or object 256; attenuation along each line is a line integral of attenuation coefficients at multiple points in the patient or object 256 along the line as further described therein. Each detector element receives a signal that represents a sum of radiation along each line (and thus a function of each line integral of attenuation coefficients) 260, 262 from active radiation sources that illuminates that element 264. Signals from detector elements 254, 264, are passed to the pre-reconstruction inversion processor 266, which is implemented as inversion firmware 118 in memory 116 executing on processor 266 to provide sinogram data to a reconstruction processor 268 implemented as reconstruction firmware 122 in memory 116 executing on processor 268 to provide images. In alternative embodiments, the pre-reconstruction inversion and reconstruction are implemented by separate firmware routines in a common image processor.

Figure 3:
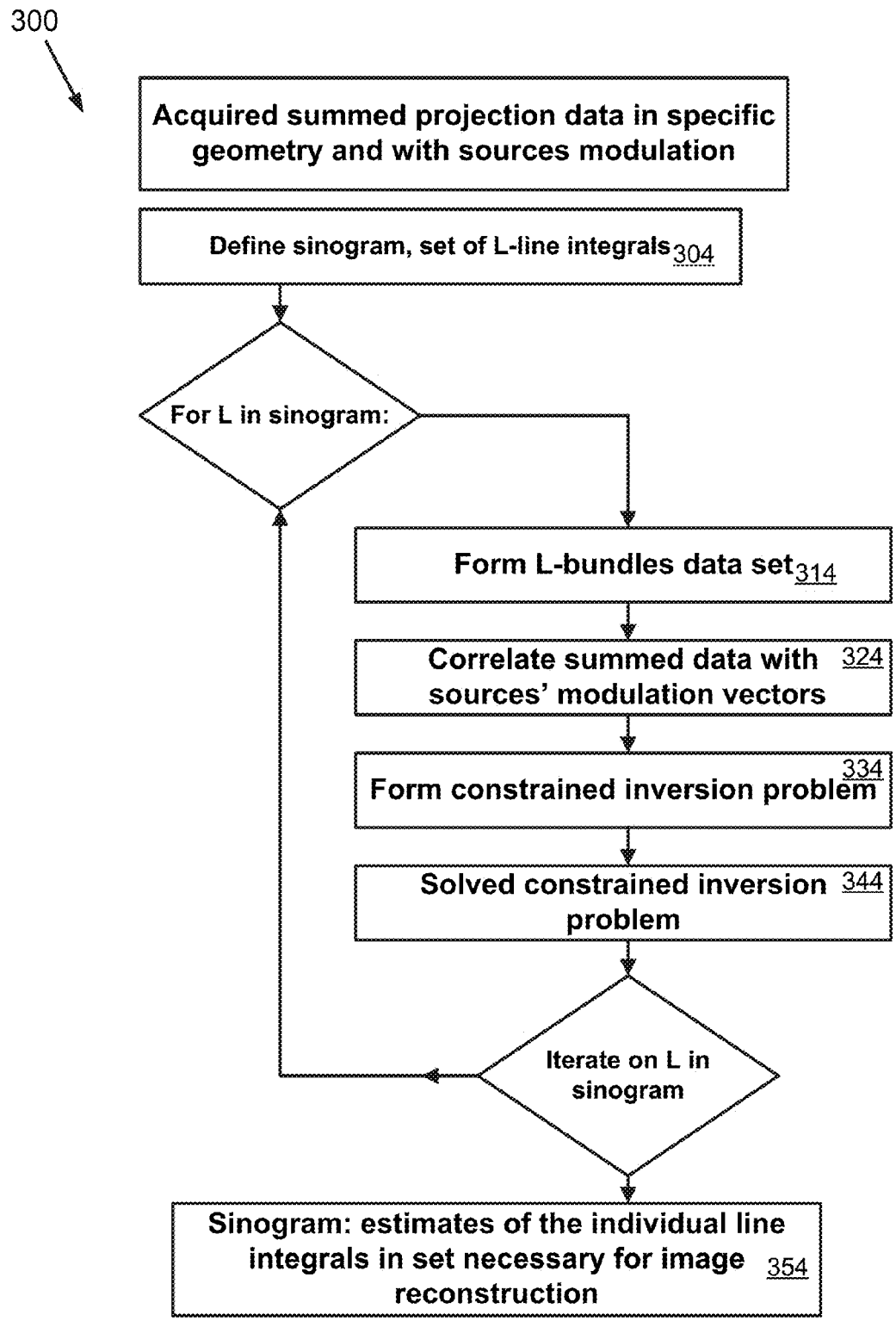
FIG. 3 illustrates in flow-chart form the tasks performed by the pre-reconstruction inversion processor.

Tasks performed by pre-reconstruction inversion firmware 118 are illustrated in FIG. 3. Since, in CT scanning systems of the present invention, projections on detector array 108 from two or more radiation sources 252 may overlap, meaning that one or more radiation detector elements 254 receives direct un-scattered radiation from two or more of sources 252, the line integral signal contributions from each source as received at the radiation detector elements 254, 264 must be separated to produce a sinogram that can be processed with conventional image reconstruction firmware 122. In order to do so, the inversion firmware 118 determines set of lines L (sinogram 304) for which individual measurement estimates need to generated for conventional image reconstruction to proceed. Generally these lines correspond to lines 258, 260 associated with paths from each radiation source 252 and each radiation detector element 254, 264, although in specific embodiments the two sets may not correspond exactly, but only approximately. For instance, in one embodiment, the set of lines acquired in summed measurement is, as described below, a super-set of the set of lines needed for image reconstruction. Those lines L associated with each detector element 264 are grouped into an "L-Bundle 314" or group of related lines. The ensuing L-bundle is then inverted 344, or solved, either locally or globally over the entire set of lines required for each tomographic image reconstruction, separating the radiation detector total readings into separate contributions associated with each individual line of the L-bundle; these separate contributions are then associated with the corresponding lines in the sinogram 354 to provide for image reconstruction. The inversion or solving operation 344 uses as constraint 334 the correlation information 324 obtained by correlating the summed projection data with the source parameter modulation vectors. It is understood that, in certain embodiments, the line-bundle for any line L consists substantially of the entire summed projection data set associated with one tomographic slice to be reconstructed; and the constrained inversion problem applies directly to that entire slice-related data set in a "global" pre-reconstruction inversion. In other embodiments, L-bundles can be formed that relate to a significantly smaller subset of the acquired data, and pre-reconstruction inversion is performed "locally" on the limited sub-sets; in such a manner that obtaining an estimate for line-integral L involves solving a system of equations with at most as many rows (measurements) as there are radiation sources in view of the detector for the measurements.

Figure 4:
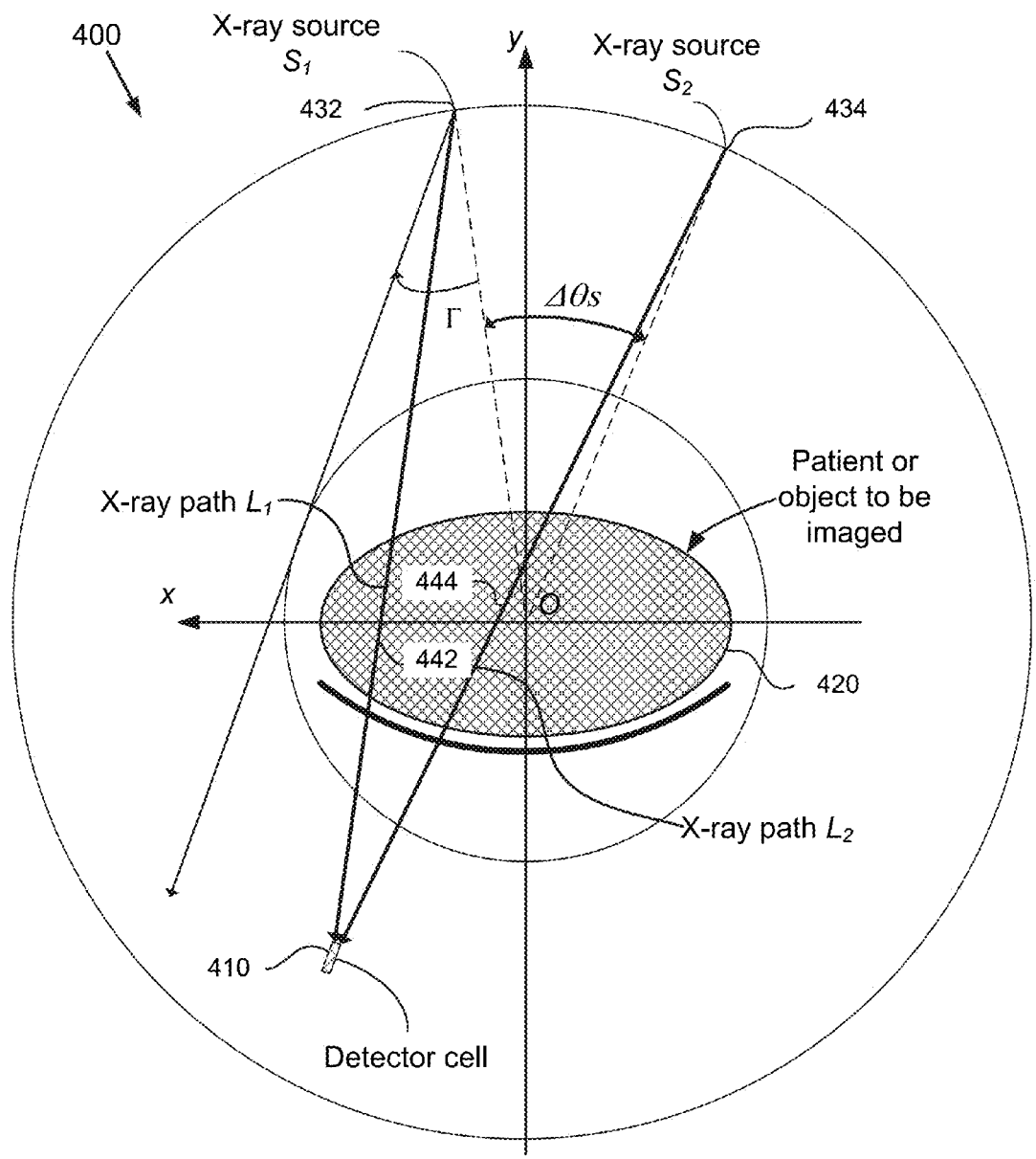
FIG. 4 presents a detector cell simultaneously exposed by radiation originating with two separate sources in a CT system, according to an embodiment.

FIG. 4 presents 400 an X-ray detector cell 410 being simultaneously exposed through a patient or body 420 to be imaged by two spatially separated X-ray sources $S_1$ 432 and $S_2$ 434, at a given moment in time (sources not shown). According to Beer's law, the detected primary beam intensity is then:

$$I = \int_{Energies\ E} \{I_{0,1}(E)\exp(-\int_{Path\ L_1}\mu(l,E)dl) + I_{0,2}(E)\exp(-\int_{Path\ L_2}\mu(l,E)dl)\} \quad (1)$$

where $I_{0,1}$ and $I_{0,2}$ are the intensities impinging on the object from sources $S_1$ and $S_2$ respectively, and $\mu(l,E)$ represents the object's linear X-ray attenuation coefficient as a function of energy E along paths through the body, the paths considered here being paths $L_1$ 442 and $L_2$ 444 respectively from sources $S_1$ 432 and $S_2$ 434 to the detector cell 410. Since as discussed previously, X-ray sources are generally broad-band, an integral over the sources energy E is necessary to properly model a measurement.

Figure 5:
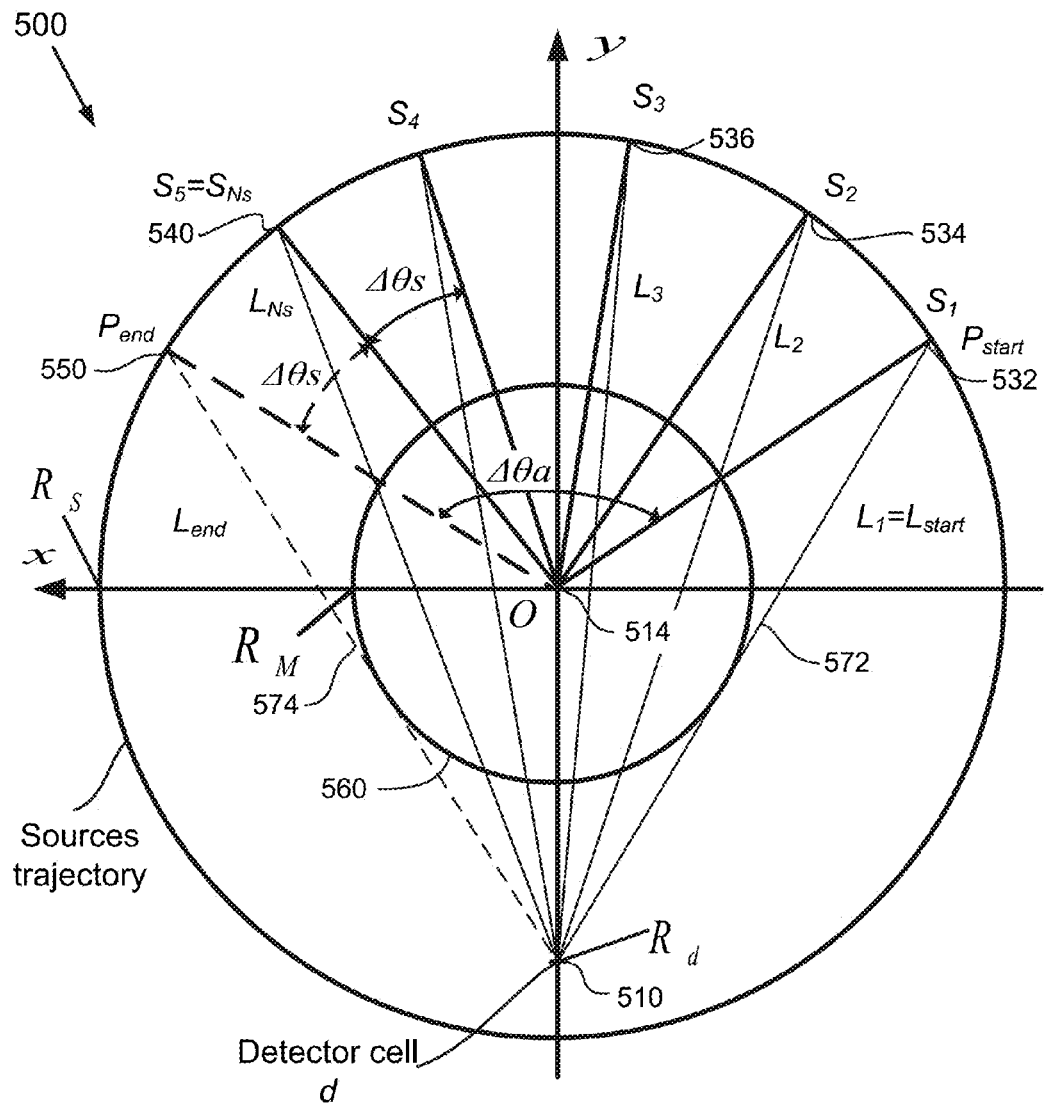
FIG. 5 presents a detector cell simultaneously exposed by radiation originating with five equispaced separate sources in a CT system, according to an embodiment, and illustrates a geometric condition for local pre-reconstruction inversion, in one embodiment.

More generally FIG. 5 presents 500 an X-ray detector cell 510 located at distance $R_d$ from isocenter O 514 being simultaneously exposed through a patient or object to be imaged (not shown) by a multiplicity of spatially separated X-ray sources $S_1$ 532, $S_2$ 534, . . . , $S_{Ns}$ 540 at a given moment in time (Ns=5 illustrated). The figure also illustrates the general condition for the associated system of equations to be locally solvable: If the equidistributed (in central angle) $N_S$ sources set were extended with the addition of one additional source at point $P_{end}$ 550 in the figure, then, the extra source would not contribute an additional path through the object to the given detector cell. That is, $N_S$ sources contribute $N_S$ paths traversing the field-of-view of radius $R_M$ 560, but ($N_S$+1) equidistributed sources (with the same source-to-source central angle separation) still contributes only $N_S$ paths through the measured field-of-view; the additional path would be traversing a region outside the circle of radius $R_M$, and thus contributes only an air measurement— or no additional measurement if the sources are collimated on the source side to irradiate only the measured field-of-view. In specific geometries, this additional source is such that the two extreme sources (of the extended set including the one additional source at point $P_{end}$ 550) projections through the measured field-of-view do not overlap on the detector. (It is noted that the figure illustrates the limit condition with the two lines $L_{Start}$ 572 and $L_{end}$ 574 from the extreme sources of the extended source set are just tangent to the measured field-of-view of radius $R_M$ 560). It is also noted that the constrained, regularized pre-reconstruction inversion methods of the present invention apply whether or not the individual line recovery problem is locally solvable.

Figure 6:
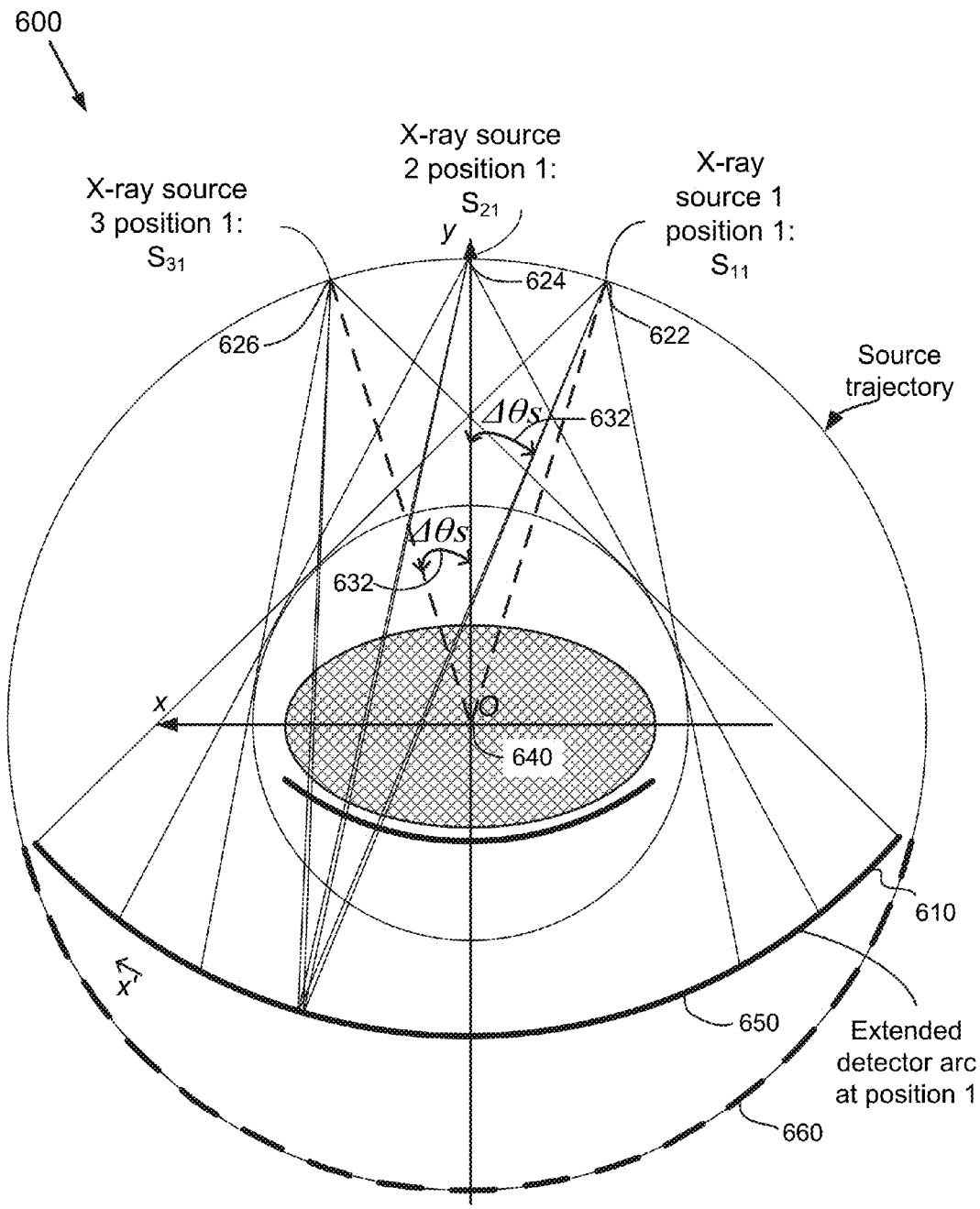
FIG. 6 shows a third generation CT system with three X-ray sources mounted on the same gantry as the detector, the sources being simultaneously active and illuminating the detector, according to an embodiment.

In FIG. 6 a CT system 600 with a rotating gantry (not shown) supporting a detector array 610 and three X-ray sources 622, 624, 626 is presented. The geometry is similar to that of a typical third-generation CT system except that three X-ray sources are mounted on the gantry, generally facing the detector. In a preferred implementation their spatial separation is determined in part by the geometry and extent of the detector array and in part by the specifics of the data acquisition. In particular it is preferable for the sources to be equispaced in central angle: any two of the sources (which may not be in the plane of the figure) are separated by an angle $\Delta\theta_s$ 632 as measured from the system isocenter 640 (a "central angle" $\Delta\theta_s$), and the parameters of data acquisition selected such that the central angle separation between any two sources corresponds to a multiple of the central angle $$\Delta\theta_V = \frac{2\pi}{N_V}$$

between two adjacent gantry positions, corresponding to acquisition of two adjacent (in gantry rotation angle) projections ($N_V$ views/projections per 360-degree rotation). The trace 650 of the detector array 610 shown in FIG. 6 is substantially centered on the central source 624, or on the intersection of a line from the detector center through isocenter with the source trajectory on the source side, if there is no central source; it is assumed as usual that any X-ray beam through the measured field-of-view originating at one of the provided sources intersects the detector arc on the distal end of the beam. It is understood that the detector retained in a system designed for simultaneous exposure by two or more X-ray sources may have a shape, position, and extent specific for the targeted application. In an embodiment, the detector trace arc is located on the geometrical arc corresponding to the trajectory of the sources, as shown by dashed line 660 in FIG. 6.

Figure 7:
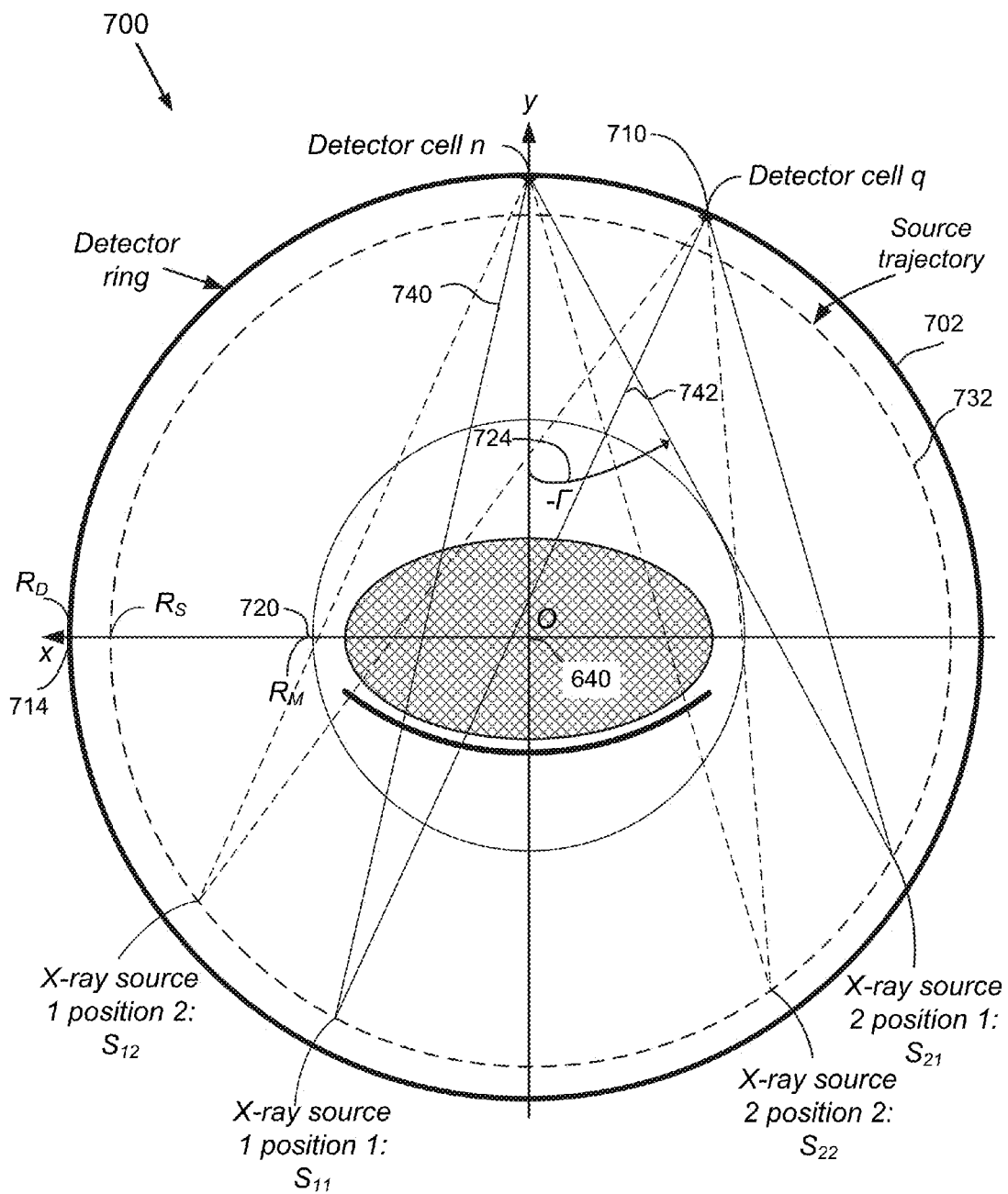
FIG. 7 illustrates a CT system in a geometric configuration similar to fourth generation CT, except that two X-ray sources are rotating around the patient and simultaneously exposing the patient and part of the detector, according to an embodiment.

FIG. 7 illustrates a multi-source imaging system design 700 similar to that of fourth-generation CT. In this geometry, X-ray sources rotate inside an outer radius defined by a fixed gantry 702 onto which an array of detector cells 710 is arranged. The detector array arc at radius $R_d$ 714 commonly covers 360-degrees (a full circle), or, in specific systems such as "Electron Beam Tomography," an arc nominally equal to 180-degrees plus the full X-ray fan angle necessary to cover the entire measured field-of-view of radius $R_M$ 720 (that is at least ($\pi$+2$\Gamma$) radians; in fourth-generation geometries, $$\Gamma = \operatorname{asin}\left(\frac{R_M}{R_d}\right) \text{ 724).}$$

The source typically rotates on a circle of radius $R_S$ 732, with $R_S < R_d$. Detector-based fan-beam projections 740, 742 . . . , are acquired over time, as the X-ray source(s) travels opposite the patient with respect to a particular detector cell. Additional CT embodiments include systems with multiple X-ray sources, or arrays of X-ray sources, substantially distributed over an angle covering up to ($\pi$−2$\Gamma$) radians in central angle, and rotating within the fixed detector.

Figure 8A:
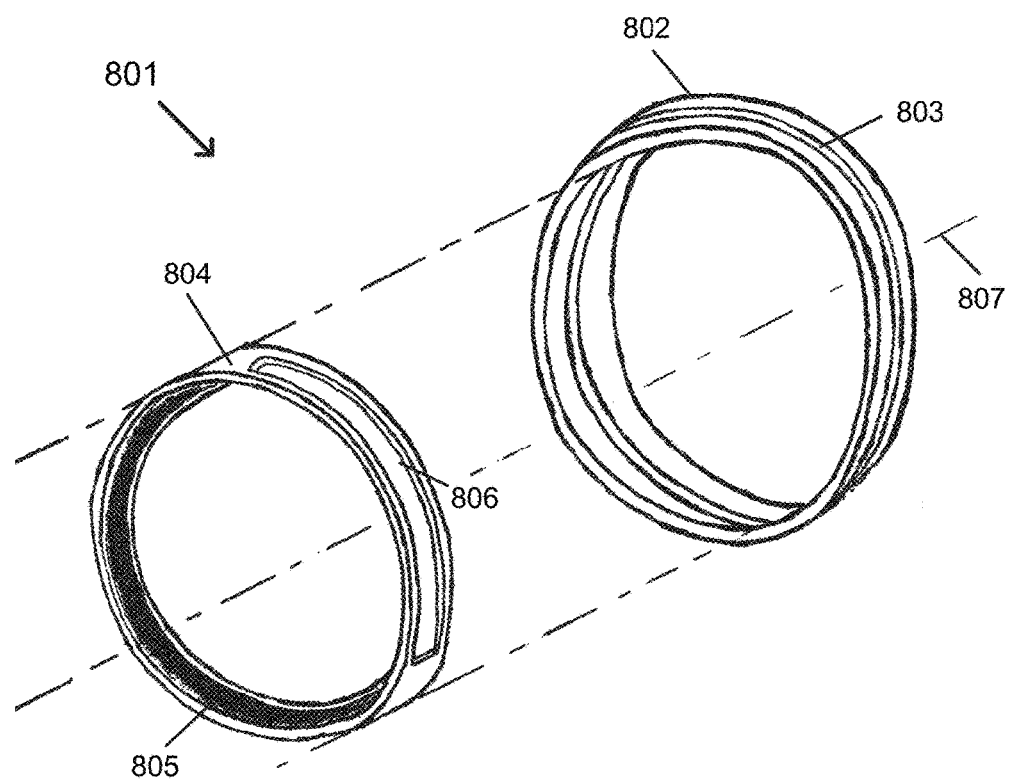
FIG. 8A presents a dual-drum CT system with a flying detector rotating within an external source gantry, the source gantry being either fixed or rotating depending on the embodiment.

In another embodiment, and as illustrated in FIG. 8A, a CT system is provided with two concentric gantries 801 or "drums," the exterior drum 802 supporting a multiplicity of X-ray sources (not shown) and the inner drum 804 comprising a detector array 805 and an extended aperture 806 through which X-rays from the outer drum sources illuminate the object or patient to be imaged (a "flying detector"). The source gantry 802 may be fixed or itself rotating within a fixed frame (not shown) depending on the embodiment. Source gantry 802 may support multiple discrete sources or tubes; or multiple source arrays. In one embodiment an elongated aperture 803 is provided for the beams from the sources mounted on the external surface of gantry 802 to radiate through the gantry and onto the object to be imaged and detector. In other embodiments (not shown), a set of discrete apertures is provided, one facing the exit port of each of a plurality of X-ray tubes. When two or more X-ray sources are illuminating the body through the detector drum aperture 806, their projections may overlap at least in part, and the area of projections overlap in turn illuminates a portion of the radiation detector 805. Since in general the two drums rotate at different angular velocities, the area of the detector simultaneously illuminated by two or more sources varies in time. In operation, at least one of the gantries 802 and 804 rotates with respect to rotation axis 807. The rotation direction and angular velocities of the two respective gantries can be set independently from one another.

Figure 8B:
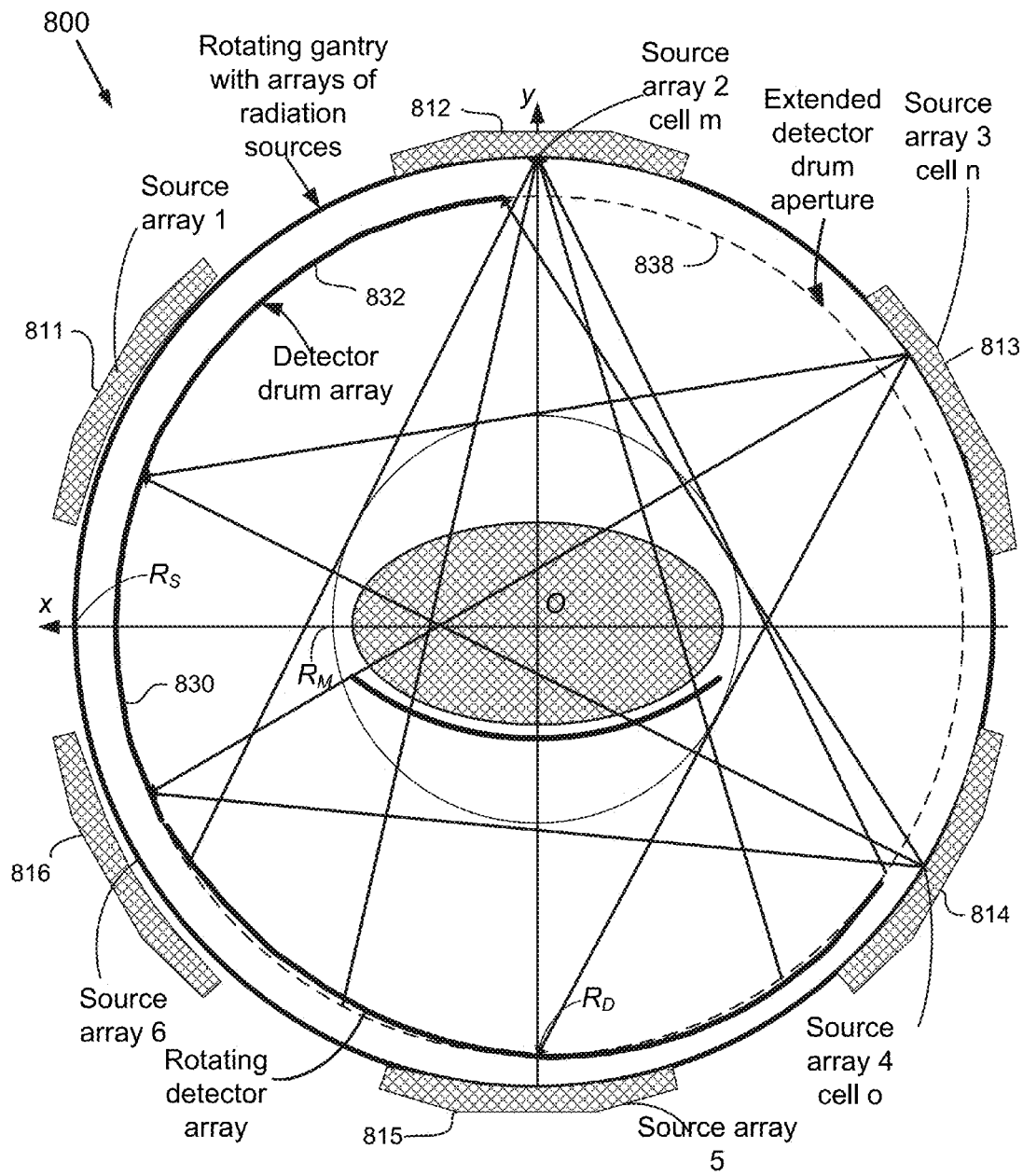
FIG. 8B shows a diagram view of a CT system with an external X-ray source drum rotating at a first angular velocity $\omega_s$, and an internal X-ray detector drum rotating at a second angular velocity $\omega_d$, the source drum supporting a plurality of source arrays, according to an embodiment.

FIG. 8B schematically presents key elements of such a CT system 800, with source arrays 811-816 instead of individual source/source tubes, such that the sources are arranged on arrays distributed over substantially a 2$\pi$ radians arc. On the detector drum 830, the detector array 832 covers substantially an arc of about ($\pi$+2$\Gamma$) radians in central angle and the extended aperture 838 substantially a complementary arc of about ($\pi$−2$\Gamma$) radians in central angle.

Thus such a CT system embodiment presents a plurality of X-ray source arrays mounted on a first, external, rotating gantry or drum, and one or a plurality of detector arrays mounted on a second, internal, rotating gantry or drum. In specific embodiments of this CT system architecture, and as shown in FIG. 8 in the planar cross-section through the main plane of the gantry, at all times two or more X-ray source arrays present individual source elements that are simultaneously "in view" of the detector through the detector drum aperture 838; and upon being activated, these two or more source arrays can simultaneously irradiate a portion of the X-ray detector. The source drum rotating at a first angular velocity $\omega_s$, and the internal X-ray detector drum rotating at a second angular velocity $\omega_d$, when $\omega_d \neq \omega_s$ the geometric relationship between the X-ray sources projections on the detector drum and the detector itself varies in time. The nominal X-ray sources that are in view of the detector vary in time; in the precise position illustrated in FIG. 8, source arrays $AS_2$ 812, $AS_3$ 813 and $AS_4$ 814 are in view (or partially in view) of the detector; assuming $\omega_d > \omega_s$ a few moments later, $AS_2$ 812 will stop being in view of the detector and will be turned off; moments later, $AS_5$ 815 will start being in view of the detector and will be activated; and so on. The precise timing of source elements firings in a given source array depends on the specific of the geometry and on the acquisition parameters.

Thus generally the characteristics of CT systems for the present invention are as follows:

(C.1) As in a 4$^{th}$-generation CT, the detector is (preferably) mounted on an array centered on the system isocenter. [However it is not necessarily stationary, as is the case in 4$^{th}$ generation systems.] The central angle sustained by the detector arc is substantially equal to $(\pi+2\Gamma)$ when rotating with the sources; $2\pi$ when stationary.

(C.2)] The $N_S$ X-ray sources sustain a central angle less or equal to $(\pi-2\Gamma)$, if the CT system embodiment has a single rotating gantry. If the system has a flying detector, the subset of K sources among Ns system sources that are simultaneously active sustain a central angle less or equal to $(\pi-2\Gamma)$. This condition, together with (C.1), implies that the sources projections can cover the entire field-of-view to be measured without truncation (C.3) It is convenient for simplicity of exposition [but not necessary] that the detector radius be equal or approximately equal to the source radius: $R_d = R_s$.

(C.4) The $N_S$ X-ray sources are mounted equidistributed in central angle $\Delta\theta_s$ and sustain a central angle less or equal to $(\pi-2\Gamma)$.

(C.5) If $N_v$ is the number of projections per 360-degree gantry rotation, then the source central angle $\Delta\theta_s$ is an integer multiple of the projection separation central angle $2\pi/N_v$.

(C.6) It is convenient, but not necessary, that the source separation central angle $\Delta\theta_s$ also be an integer multiple of the detector cell central angle $\Delta\theta_d$ (central angle between two adjacent detector cells).

(C.7) Flying detector: For additional temporal gains, it is useful to consider a system comprising a "flying detector," that is a detector and system satisfying conditions (C.1)-(C.6) where additionally the detector is mounted on its own gantry/drum, separate from the sources. Then (C.3) can only be approximated.

Figure 9:
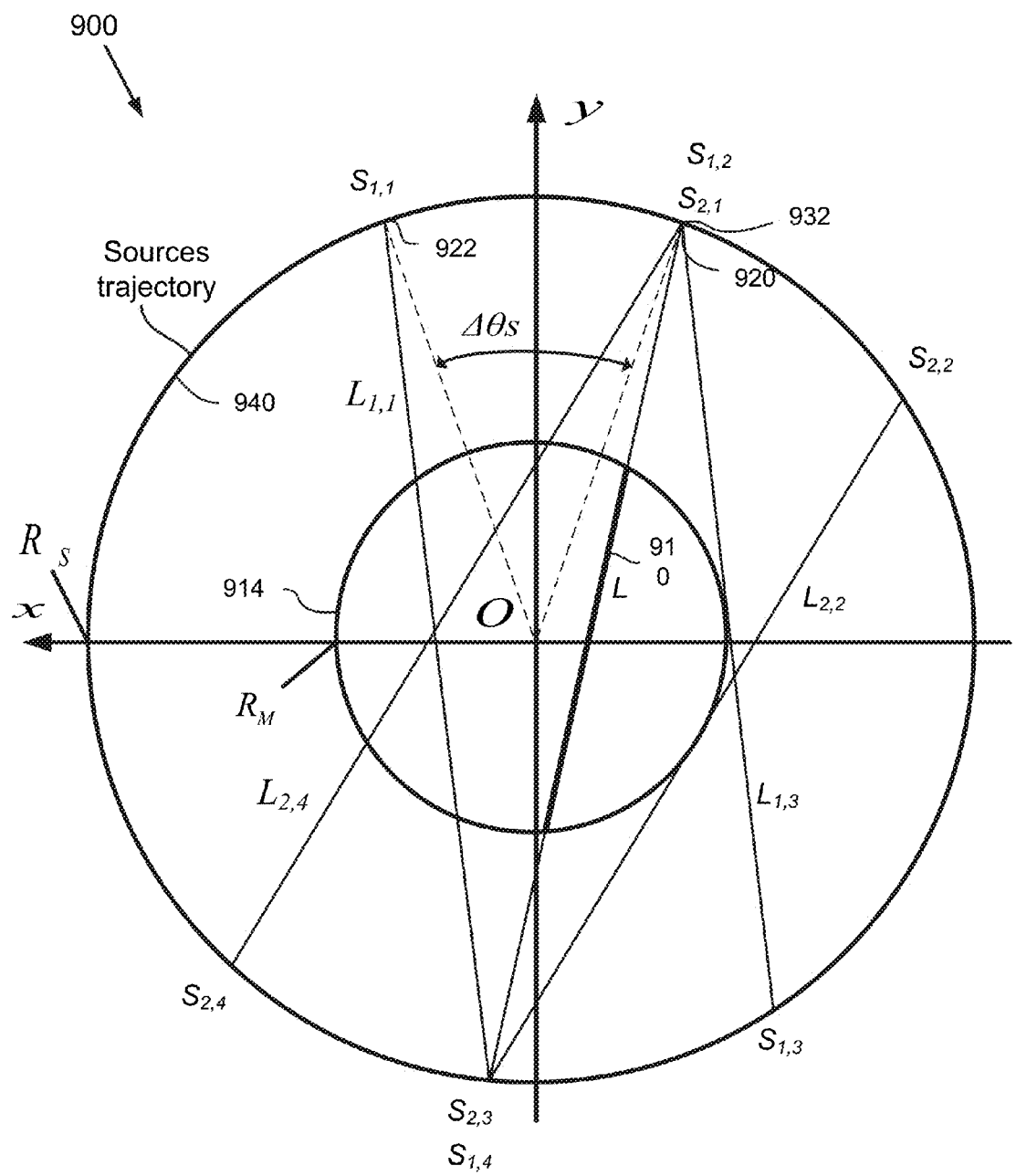
FIG. 9 shows the sampling configurations for one line path L through the object for a CT system with two X-ray sources during one gantry rotation.

FIG. 9 illustrates 900 the sampling conditions for an arbitrary line L 910 through the object (not shown) contained in cross-section in a field-of-view of radius $R_M$ 914, as obtained after a full $2\pi$ radians source-gantry rotation of a CT system with two X-ray sources 920 and 922; the two sources projections through the measured field-of-view of radius $R_M$ overlapping at least in part on the detector (not shown). Assuming a clockwise gantry rotation, line L 910 is first traversed by an X-ray beam and gives rise to an associated line-integral measurement when source $S_2$ 922 is at first position $S_{2,1}$ 932. Since both sources are by design simultaneously active, the associated X-ray measurement is thus modeled by:

$$I_1(\Delta t_n) = \int_{Energies\ E} \{I_{2,1}{}^0(E,\Delta t_n)\exp(-\int_{Path\ L(\Delta t_n)} \mu(l,E)dl) + I_{1,1}{}^0(E,\Delta t_n)\exp(-\int_{Path\ L_{1,1}(\Delta t_n)} \mu(l,E)dl)\}dE. \quad (2)$$

Rewriting the above equation with variables $LI(i,j,\Delta t_n)$ representing the respective attenuation coefficient line-integrals, dropping the $\Delta t_n$ symbols, and with a slight abuse of notation on L:

$$I_1 = \int_{Energies\ E} \{I_{2,1}{}^0(E)\exp(-L) + I_{1,1}{}^0(E)\exp(-LI(1,1))\}dE. \quad (3)$$

Re-writing the equation above for an effective energy $E_{eff}$, thus dropping the integral sign:

$$I_1 = I_{2,1}{}^0(E_{eff})\exp(-L) + I_{1,1}{}^0(E_{eff})\exp(-LI(1,1)), \quad (4)$$

this can be rewritten simply as:

$$I_1 = I_{2,1}{}^0\exp(-L) + I_{1,1}{}^0\exp(-LI(1,1)). \quad (5)$$

In equation (5) the term L represents the line for which we are interested in obtaining an estimate. The line-integral terms L and $LI(i,j)$ are the unknown, while the source terms $I_{i,j}{}^0$ are either under control of the system or well characterized by calibration measurements. Writing similar equations for all measurements that involve L, we get the linear system:

$$\begin{bmatrix} I_1 \\ I_2 \\ I_3 \\ I_4 \end{bmatrix} = \begin{bmatrix} I_{1,1}^0\exp(-LI(1,1)) + I_{2,1}^0\exp(-L) \\ I_{1,2}^0\exp(-L) + I_{2,2}^0\exp(-LI(2,2)) \\ I_{2,3}^0\exp(-L) + I_{1,3}^0\exp(-LI(1,3)) \\ I_{1,4}^0\exp(-L) + I_{2,4}^0\exp(-LI(2,4)) \end{bmatrix}. \quad (6)$$

This is a linear system of four equations in five unknown; thus it is a-priori under-determined. In this derivation, we have assumed that the line integrals that are sampled on both intersections of the path L 910 with the source trajectory 940 are the same. If that is not the case, as for instance when "quarter-offset" of the detector array is introduced to increase spatial resolution, or when X-ray source dynamic deflection is used for the same purpose, then in general the two paths differ, and the corresponding systems of equations for lines integrals L and L' (not shown; line L' is generally parallel and laterally offset by half the "line-width" defined by the cell aperture and the source(s) spatial extent) are:

$$\begin{bmatrix} I_1 \\ I_2 \end{bmatrix} = \begin{bmatrix} g_{11}I_{1,1}^0\exp(-LI(1,1)) + g_{21}I_{2,1}^0\exp(-L) \\ g_{12}I_{1,2}^0\exp(-L) + g_{22}I_{2,2}^0\exp(-LI(2,2)) \end{bmatrix} \quad (7)$$

$$\begin{bmatrix} I_3 \\ I_4 \end{bmatrix} = \begin{bmatrix} g_{23}I_{2,3}^0\exp(-L') + g_{13}I_{1,3}^0\exp(-LI(1,3)) \\ g_{14}I_{1,4}^0\exp(-L') + g_{24}I_{2,4}^0\exp(-LI(2,4)) \end{bmatrix} \quad (8)$$

In either case it is noted that the systems of equations are under-determined, that is there are fewer equations than unknown, and thus solutions cannot be completely determined without additional information.

Figure 10:
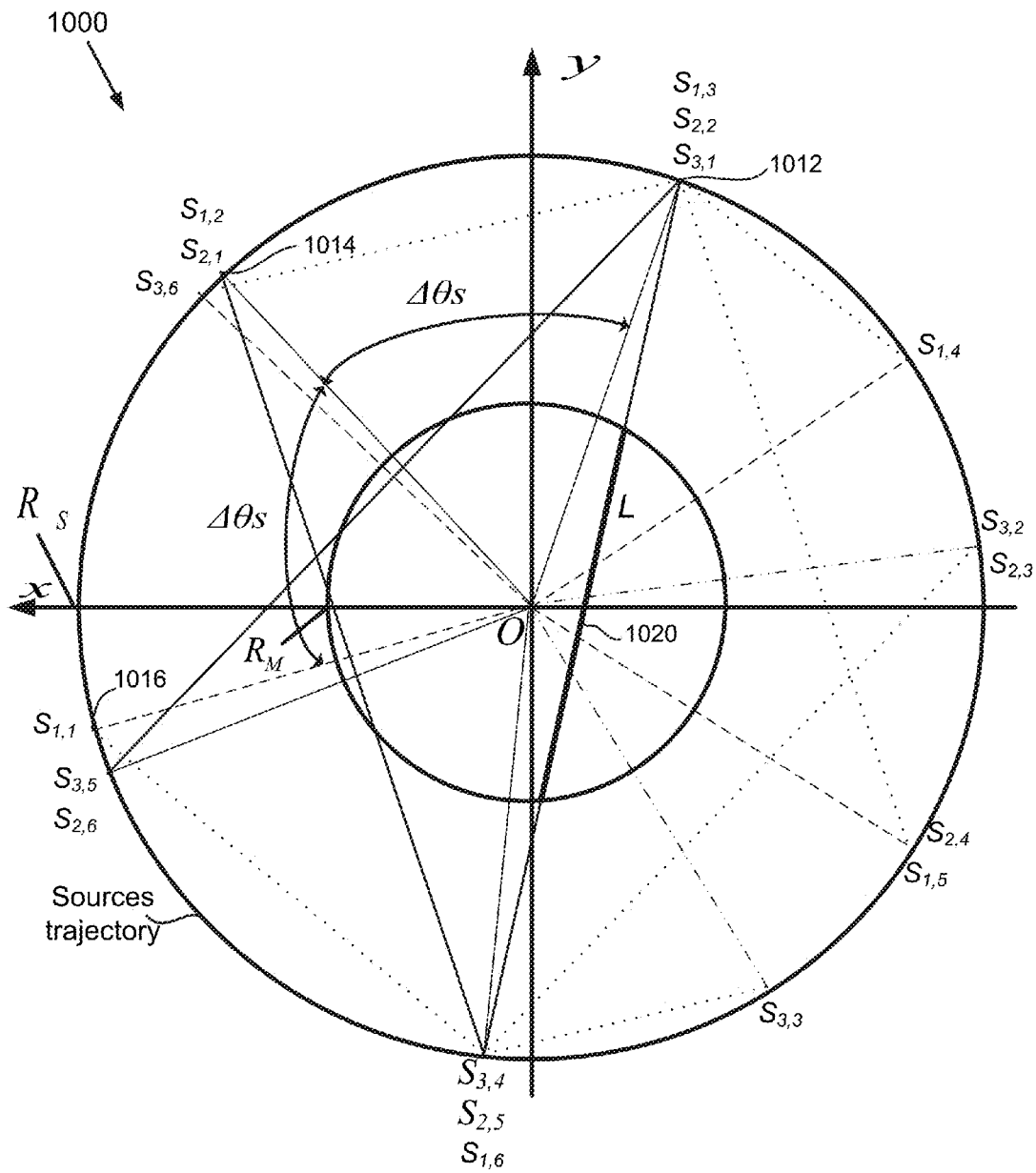
FIG. 10 is similar to FIG. 9, except that the system has three X-ray sources simultaneously active.

However as we show below, the complete set of measurements obtained after one full gantry rotation is not underdetermined; and thus using techniques of linear algebra, including regularization if needed, the complete resulting system can be inverted or solved. The considerations of the following sections apply specifically to multi-source CT systems with a single rotating gantry. FIG. 10 illustrates 1000 a CT similar to that of FIG. 9, except that three X-ray sources 1012, 1014, 1016 are mounted on a gantry over a central angle less or equal to $(\pi-2\Gamma)$ radians. For a given path L 1020 through the measured field-of-view, similar arguments would lead to the writing of two linear systems; each system having three rows (one for each measurement/ source gantry position) and relating each measurement to a set of line-integrals through the object.

Now considering the sampling that occurs in a full rotation, and denoting by $N_V$ the number of source projections over 360 degrees (for one source); i.e. $N_V$ gantry positions and associated set of measurements per full rotation), and by M the number of samples per projection/gantry position. In a typical medical CT scanner, M is of the order of 1,000 and $N_V$ is also of the order of 1,000. In the geometry of the system(s) with an extended detector arc, M is larger, as much as twice the conventional number if the detector arc is twice that of a typical third-generation CT detector; and so forth. We set the source separation angle $\Delta\theta_s$ such that it is a multiple of the source angular sampling $\Delta\theta_v$:

$$\Delta\theta_s = k_1 \frac{2\pi}{N_V} \tag{9}$$
$$= k_1 \Delta\theta_v. (k_1 \text{ integer}).$$

When condition (9) is satisfied, then the number of nominal source positions around the body remains $N_v$; each of those individual source positions is occupied at different times by source $S_1$ to $S_{N_S}$ (for a system with $S_{N_S}$ sources) in a complete 360-degree gantry rotation. In CT the angular sampling between detector cells is typically finer than the angular sampling between detector views; by a factor of about three to four. In the following description we then assume that given lines L as indicated in FIG. 9 are indeed sampled multiple times (four times over a full gantry rotation for a system as in the figure). The total number of lines (and thus line-integrals) to be measured is ($N_V/2 \times M$) since each line measured during a half rotation is assumed measured again during the second half rotation, as shown in FIG. 9. Thus for each one of these lines we collect four measurements involving a subset of four additional lines taken from the same set. Therefore, after one full gantry rotation, we have obtained ($M \times N_V$) measurements in ($N_V/2 \times M$) unknowns; and thus the complete system corresponding to writing (6) for each unknown line is NOT under-determined. In the geometry of the system of FIG. 9, to obtain samplings for the same line L from source positions $S_{1,2}$ and $S_{2,1}$, we impose that the angular increment $\Delta\eta$ between detector cells measured as a central angle be a divisor of $\Delta\theta_v$:

$$\Delta\theta_v = k_2 \Delta\eta, \tag{10}$$

Where, as indicated above, the integer $k_2$ is of the order of 3 or 4 in a typical system.

The above discussion ignores the effect of "quarter offset." In a third generation CT system a quarter offset of the detector cell is introduced along the detector arc, so that after half a rotation, ray sampling in the plane of interest overlap by about half of their width, as is known in the art. In such a configuration, the sampling from the conjugate views (the two or more views giving rise to samplings from opposite ends of the line L) do not bring about a second sample for a given line-integral; but rather gives a sample for different set of lines, thus increasing the CT system spatial resolution. This is equivalent to stating that after a full rotation, a set of ($M \times N_V$) lines is measured. The argument of the above paragraph applies again, and after a full rotation we obtain a set of ($M \times N_V$) measurements in ($M \times N_V$) unknowns; which is thus amenable to inversion techniques to recover the line-integral terms that are the inputs to the standard image reconstruction processes. Thus because a geometric set of line-integrals associated with a particular plane is sampled $N_S$ times, for a system with $N_S$ sources, the number of unknowns remains less or equal to the total number of separate measurements; each separate measurement involving a multiplicity (up to $N_S$) of sources.

Similarly, should the gantry rotation be limited to a half-scan rotation, the system will in effect (after rebinning to parallel projections) measure a set of approximately ($N_V/2 \times M$) measurements in ($M \times N_V$)/2 unknown, thus again lending itself to inversion.

Further it is noted that the linear systems obtained are sparse: Each row of the system involves only $N_S$ unknown terms; sparse systems are known to be more amenable to inversion; with fewer instability problems.

The above discussion generalizes featuring a CT system with $N_S$ sources generalizes to a CT system with K simultaneously active sources; whether the K be discrete sources or K active elements of source arrays with potentially a much larger number $N_S$ of source points. That is, for a full rotation of such a system, under specific geometric conditions similar to those outlined above concerning the sources angular separation and the detector cells angular separation, and the view angular separation, a system of ($M \times N_V$) measurements in ($M \times N_V$) unknowns is obtained; each line in the linear system (linear in the exponentials of the unknown) includes K non-zero entries. Thus, simultaneous irradiation by K sources leads to a system with as many or fewer unknowns than measurements, that is a problem amenable to regularized inversion in CT. An exemplary embodiment for such a system having a flying detector rotating inside a source gantry with a plurality of source arrays.

In general, it is the case also that, for a system with K simultaneously active sources, when the extreme sources central angle separation meets the condition described with reference to FIG. 5, then the linear system of equations associated with the measurement is directly and locally invertible, that is, we do not require data from a full rotation data acquisition to recover individual line integral estimates.

Thus after a complete effective rotation, $M \times N_V$ measurements will have been acquired relating a total of $M \times N_V$ individual line-integral unknowns; each measurement involving up to K summed line-integral measurements from up to K different sources. As described above since in most embodiments K<min{M, $N_V$} the system is sparse. It is thus either directly invertible, or amenable to traditional regularization techniques enabling estimates of the line-integral terms to be obtained. Practical inversion of such a large system is typically performed via iterative techniques, as is known in the art. Such methods allow the use of statistical models and a-priori information, as well as the use of regularization terms, in the inversion problem. Such techniques are described below.

Consider more generally a computed tomography system with Ns sources mounted on a rotating gantry. At any given instant in time, a subset K of sources is active (possibly the subset is equal to the full set), with central angle between the two extreme sources in the subset of K sources is less or equal to ($\pi - 2\Gamma$) radians. At any given position of the gantry, the projections of the sources through a measurement field-of-view of radius $R_M$ expose a total of M detector cells, as measured along the detector arc (if the detector as several rows along z, then this number M is substantially multiplied by the number of rows). Independently of $N_S$ and K, the number of measurements at one gantry position/one sampling interval $\Delta t$ is equal to M, corresponding to up to $M \times K$ line integrals. When the system acquires $N_V$ projections per $2\pi$ gantry rotation, then the total number of measurements is $N_V \times M$ (for one tomographic slice of interest), corresponding to up to $N_V \times M \times K$ line-integrals. Thus the system is a-priori under-determined, and the method described below can be applied to regularize the inversion.

However, when conditions (C.3) and (C.4) described above are met, the set of unknown line-integrals corresponding to the measurements is reduced to $N_V \times M$ lines. This is because each of the K sources intersects in turn the line integrals as the first one (of the source) did. In this case, the pre-reconstruction inversion problem can be formulated as solving the following system of equations, where we write N for $N_V$:

$$[I]_{M \times N} = [A]_{M \times N, M \times N} [ELI]_{M \times N}, \quad (11)$$

where $[I]_{M \times N}$ is the vector of measured summed projection data (intensities), $[ELI]_{M \times N}$ is the vector of the exponentials of the negative of the unknown line-integrals, and the matrix A is a (large) square matrix which is quite sparse, since on each matrix row only up to K terms are non-zero. The coefficients of matrix A are given by the source intensities (as made explicit in Eq. (6), for example). Since matrix A is square, sparse, and some of the coefficients are under system control, it is always either invertible or nearly invertible—that is, amenable to regularization, for instance in the form of Tikhonov regularization, as known in the art.

There exist many ways to formulate an inverse problem such as this pre-reconstruction inversion. In a conventional least-squares approach, the inverse problem is written as:

$$\min_{ELI} \| [I]_{M \times N} - [A]_{M \times N, M \times N} [ELI]_{M \times N} \|^2. \quad (12)$$

So in general, the pre-reconstruction problem is amenable to inversion. Because noise can be amplified in any inversion problem by the inversion process, we describe two methods of constraining (or regularizing) the problem.

While in theory the linear system might be amenable to inversion, the presence of noise may render the inversion more unstable. This noise and instability increase is mitigated by the fact that the linear systems in question are sparse, as noted above. Nonetheless, it is desirable to introduce regularization techniques that will limit noise amplification in the inversion process. The present invention now introduces two such regularization techniques.

These regularization techniques are useful for CT systems in the configuration of FIG. 8, that is a multi-source CT system with independent rotation of the sources and of the detector. In such configurations, when $\omega_d \neq \omega_s$ then the number of measurements can be a-priori substantially less than the number of unknown. For example, for such a system with $$\frac{\omega_d}{\omega_s} = \frac{\Delta \theta_a}{2\pi} N_S$$

$$= \frac{\pi - 2\Gamma}{2\pi} N_S,$$

each line-integral L contributes to a measurement exactly once (with quarter offset); and twice (without quarter offset); each measurement being the sum of K line-integrals, if K sources are simultaneously active and overlapping on the detector $$\left( K = \left[ \frac{\pi - 2\Gamma}{2\pi} N_S \right] \right),$$

where in this equation [x] denotes the integral part of x). Such a system is locally significantly under-determined and requires some kind of a-priori information or constraints to be locally solved effectively.

A source modulation approach is disclosed that introduces specific temporal variation patterns in a given X-ray source. Correlation of a given detector cell or set of detector cell time-sequence of recorded signals with a source modulation pattern enables the identification and separation of the associated signal from a summed signal originating with simultaneous exposure from two or more sources. The fundamental reason for this being that the line-integral data varies relatively slowly with projection angle: that is, at least the low and mid-frequency terms in the line-integral projection data can be recovered or estimated through correlation. The output of the correlation processing consists of the apportionment of the summed signal collected by each individual cell of a detector array to each one of the simultaneously active radiation sources that contributed to the summed detector cell measurement.

Source parameters that may be modulated in time include source applied peak kilo-voltage (kVp); source tube current, typically measured in mA (mA); tube anode target material; applied filtration in front of the X-ray source(s); and beam focal-spot parameters, including shape and intensity distribution. In certain X-ray sources, the plane and direction of polarization could in principle also be modulated. Future sources, such as expanding on X-ray lasers currently only available for relatively low X-ray energies, may enable the dynamic selection of a specific energy range.

When considering two or more sources simultaneously illuminating a detector array, or part of a detector array, it is possible to modulate each X-ray source separately and in such a manner that the modulation signals are "relatively orthogonal" to each other. The availability of several source control parameters facilitates such a design.

The effects of varying two key X-ray tube control parameters, the tube current (mA) and the tube peak kilo-voltage (kVp) are as follow. A change in tube current scales the tube output at all frequencies in proportion to the change. Thus, the total intensity of tube output varies linearly with tube mA. A tube current change will not change the relative spectral distribution of X-ray as observed through any object; just the magnitude at each frequency. A tube kVp change brings into the spectrum new, higher energies (with a kVp increase) and also changes the total tube output in a proportion related to $kVp^{2 \cdot k}$, where k is a number that can be determined experimentally. A change in tube kVp will change the shape and distribution of the spectrum as observed in air, but also as observed exiting any given object that may be placed in the beam, through the process known in the art as "beam hardening." That is, different spectrum frequencies are affected differently by a change in kVp.

Specific target materials, and in particular, their respective K lines, can have a significant impact on the overall spectrum shape. The spectra can be further shaped by specific filtration; filters present their own absorption lines at which the linear X-ray attenuation coefficient presents a "discontinuity jump;" as is known for example in the rhenium (Rh) filtration of the tungsten spectrum at 30 kVp.

Figure 11:
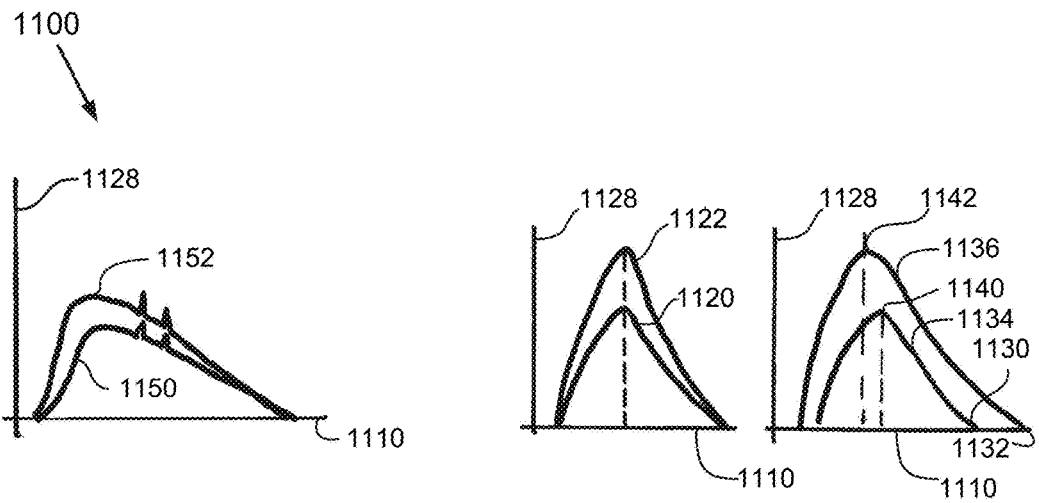
FIG. 11 illustrates X-ray spectral beam shaping by a change in tube current, a change in applied kilo-voltage, a change in beam filtration, and the result of spectral filtration on two specific spectra.
Figure 11:
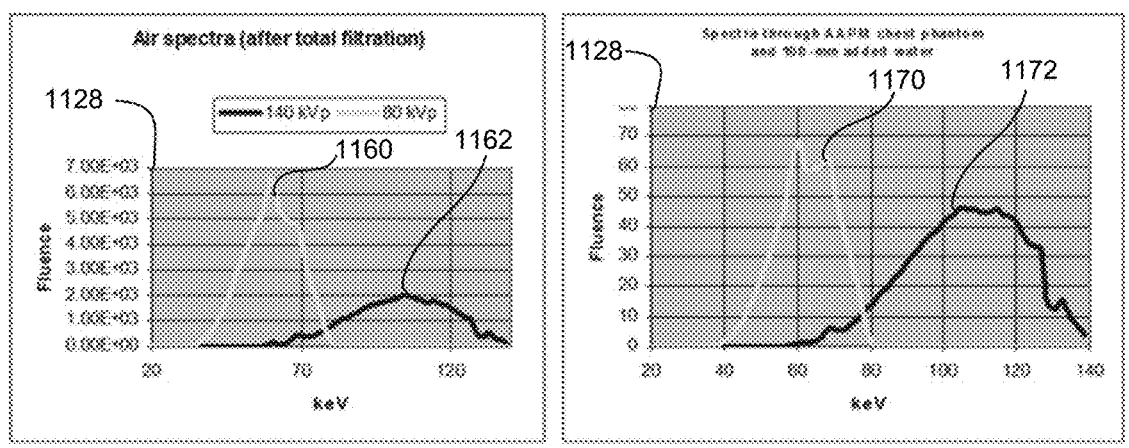

FIG. 11 illustrates schematically 1100 various source control parameters and how they can in principle be made to change in time. It is noted that in the current state of the technology, kVp changes can be effected more rapidly than mA changes. Because kVp changes induce non-linear effects in the radiation energy 1110 distribution, kVp is normally changed on a discrete set of levels—which can be chosen arbitrarily by the user. At each retained level, specific calibration data need to be acquired to properly characterize the beam and correct for various spectral effects. However, provided careful calibration measurements are made, kVp could be modulated on a fine discrete scale (possibly relying on calibration interpolated data). By contrast, mA changes can be simply calibrated by a scaling term, as illustrated by curves 1120 and 1122 showing the intensity 1128 for two spectra differing only in the amount of tube current. A change in kVps 1130 and 1132 is illustrated for two otherwise unchanged parameter sets by curves 1134 and 1136 showing displaced intensity peaks 1140 and 1142. Filtration can have a drastic effect on the beam spectral quality. As is illustrated by curves 1150 and 1152, added filtration can change the relative intensity of the beam as a function of energy. It can also introduce sudden changes/discontinuities through the K-edge effect (not shown). Curves 1160 and 1162 present two specific spectra as impinging on an object to be imaged; the effect of object filtration is shown for the associated spectra is shown by curves 1170 and 1172; note the change in intensity scale. In the current state of the technology, X-ray beam filtration typically involves various metals and thus can be provided only as a discrete set; (c.f. filter wheel; and double filter wheel: see U.S. Pat. No. 6,950,492).

Figure 12:
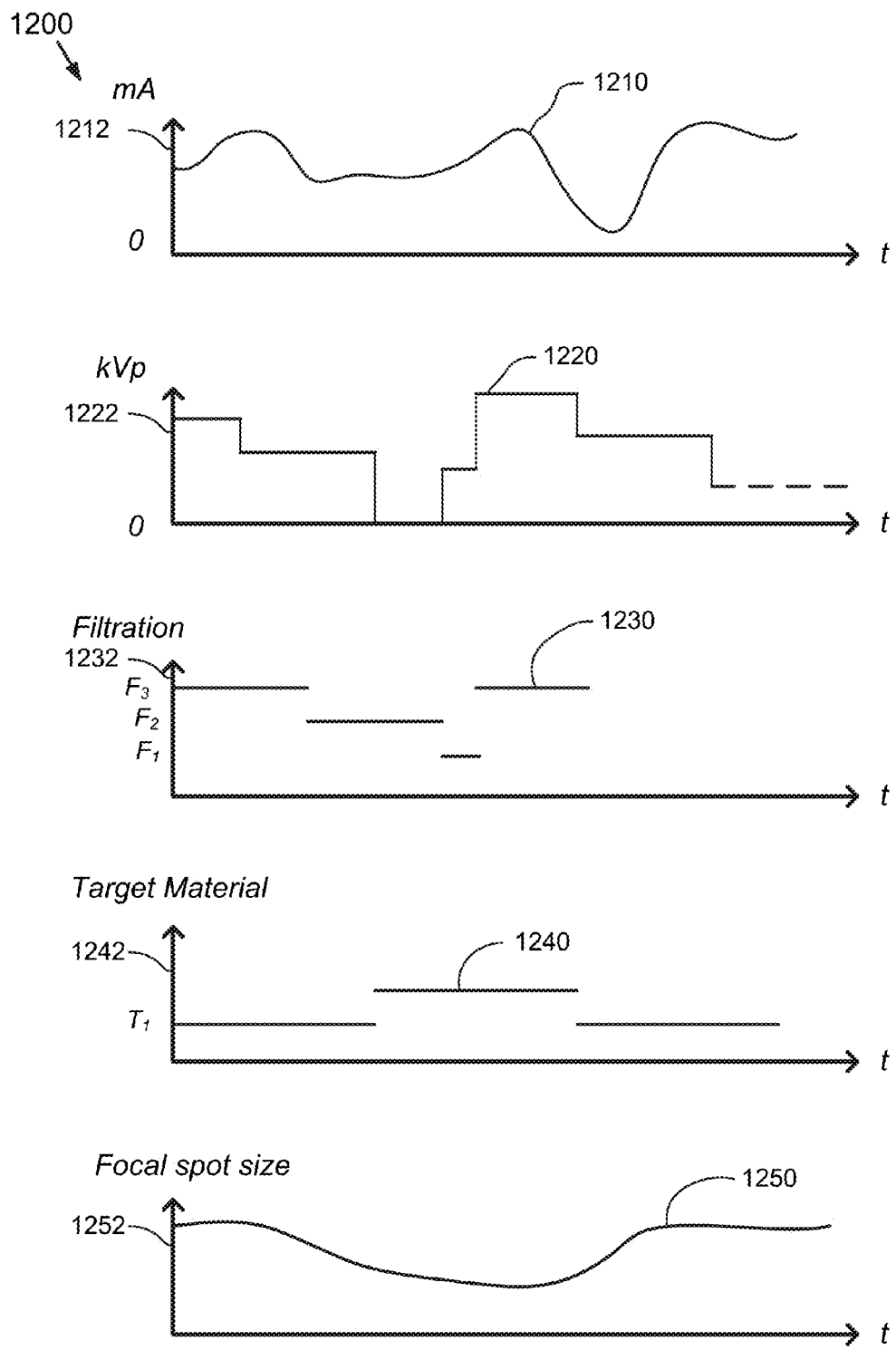
FIG. 12 presents patterns of modulation for specific source parameters selected from a set of source parameters, according to one embodiment.

FIG. 12 presents 1200 exemplary waveforms over time for various parameters controlling a given X-ray radiation source. Thus possible time evolutions 1210 for tube current 1212, 1220 for peak-kilo-voltage kVp 1222, choices 1230 of filter material and/or material combinations, target materials 1240 and focal spot size 1250 are illustrated schematically. X-ray tubes typically comprise anodes made of a single material. However, tubes that enable dynamic change in target material have been described (U.S. Pat. No. 6,973,158 for an example). Focal spot sizes are in part controlled by selection of tube current and kVp; however in certain tube designs it is also possible to control the beam size, as well as position (electron beam deflection) as it impinges on the tube target. Such control is effected by application of either electrostatic voltages, or electromagnetic fields, as known in the art.

Figure 13:
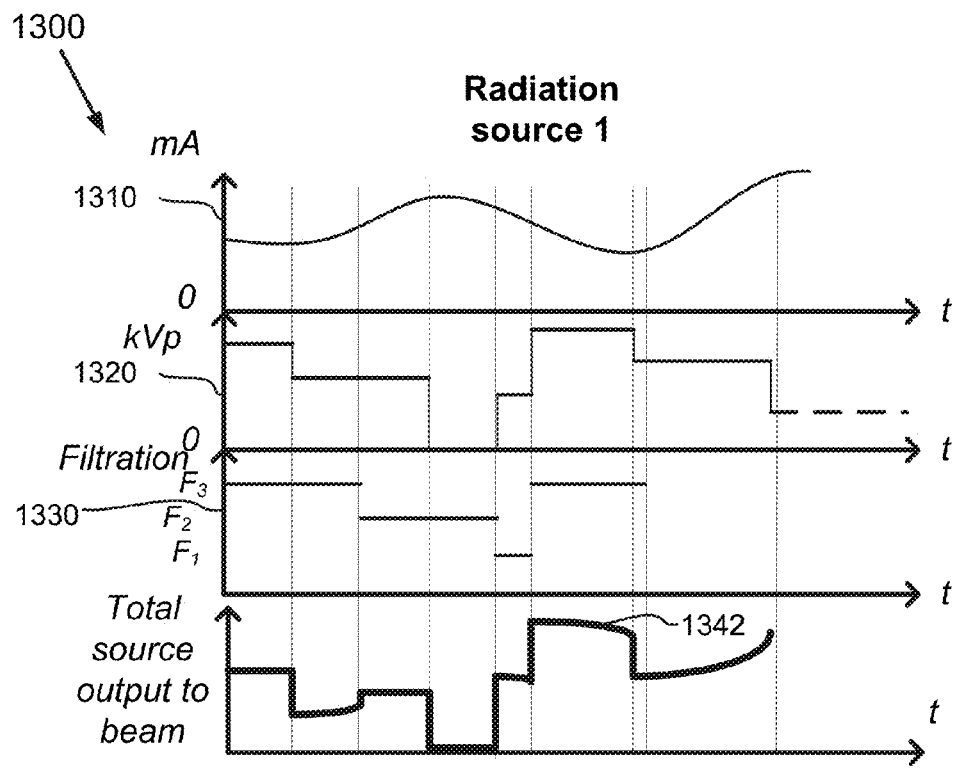
FIG. 13 demonstrates applying a time sequence of control parameters to two radiation sources, generating a single source control vector for each source, to provide source encoding for summed projection signals, thus facilitating the correlation analysis of the summed projection signals, according to an embodiment.
Figure 13:
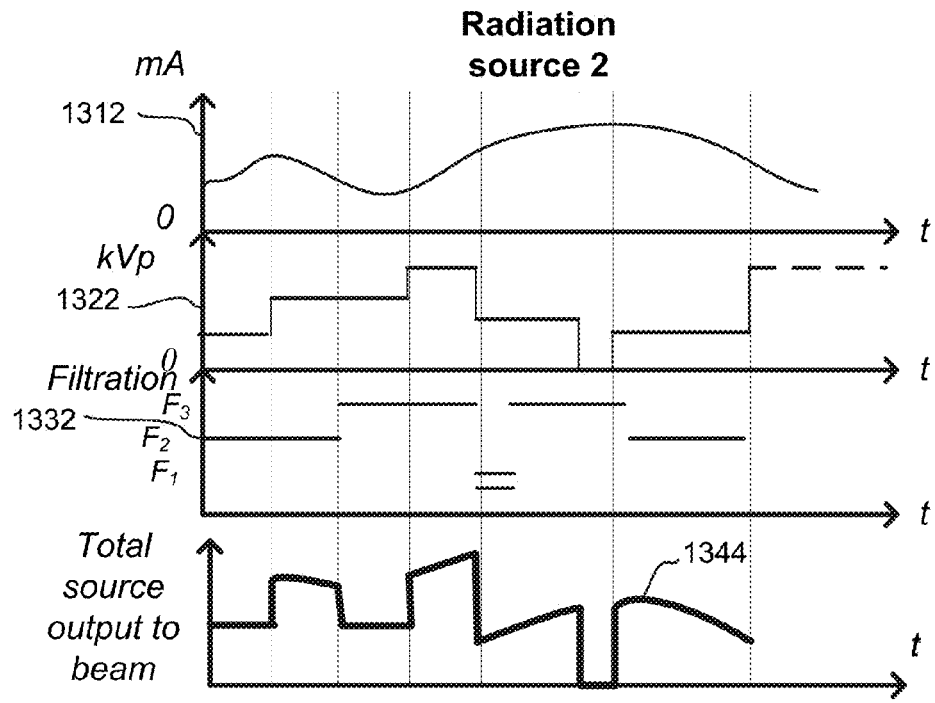

While as illustrated in FIGS. 11 and 12, various control parameters are available to shape spectra, so that two or more radiation sources could be used with relatively reduced spectral overlap in the medical diagnostic range, it is noted that time-evolution of these parameters enables coding of the projection signal generated by a given source. FIG. 13 presents an example 1300 of such source coding for two sources.

By specifically designing the time-evolution of the control parameters for two or more independent sources, it is possible to generate in a summed projection signal time-induced variations that are reflective of the respective sources. This method of time-control of a set of sources is illustrated schematically 1300 in FIG. 13, showing how two sources could be modulated such that the associated signals, in the extent they are dominated by the source correlations, could be extracted and assigned to each of the respective sources ("pseudo orthogonality"). Thus, summed projection signal correlation analysis leads to the identification of individual source signals, and to the extraction of such individual source signal estimates from summed projection data. FIG. 13 shows time evolutions for two tube currents 1310 and 1312, peak-kilo-voltages 1320 and 1322, and filtrations 1330 and 1332. Other parameters could be used to modulate the radiation beams, as discussed above. To perform correlation analysis, it is desirable to generate from the plurality of control parameters varying in time, one vector per source, that is representative of the source variations overtime. Then for each source it is necessary to correlate only one vector with the summed projection data, generated in the manner described below. One method of computing a single source parameter vector from the plurality of control parameter waveforms, is to consider the effects of each of the parameters on the total intensity generated by the source. As we have seen above, a change in tube current immediately scales the tube output by the value of the mA. A change in kVp changes the total output by a factor to $kVp^{2 \cdot k}$, where k is a number that can be determined experimentally. Given a target material, such as tungsten, there exist accurate models of tube output as a function of frequency. To generate a value representative of both the tube current and the kVp, it suffices to integrate under the curve (such as curves 1160, 1162 for example) for such a source spectrum dependent on (target material; kVp; mA). Similarly, the effect of applied filtration can be calculated by passing the above source spectrum through a filter of known material, and again calculating the integral under the spectrum curve (as could be done, for illustration, by calculating the filtered spectra integrals for curves 1170 and 1172 of FIG. 11). In so doing, we obtain a single time-dependent vector representative of the variations of the source output depending on applied parameters. Other methods of obtaining such a source-parameter representative vector exist. The output of such calculations is shown in schematic form, in curves 1342 and 1344 of FIG. 13. By appropriately controlling the various sources parameters, representative curves can be generated that present significant lack of correlation, or "relative orthogonality" over useful time-frames or time intervals.

Figure 14:
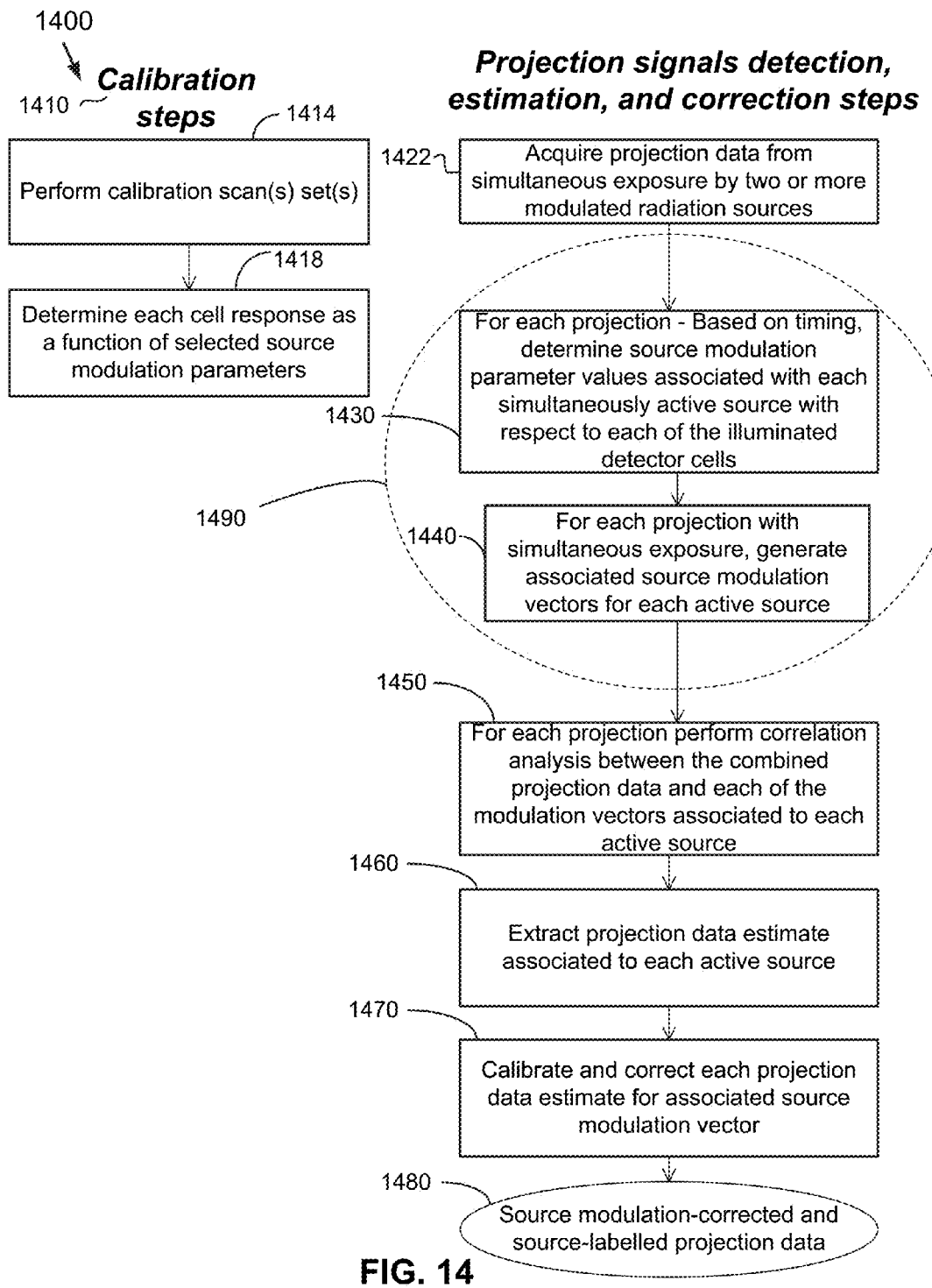
FIG. 14 is a flowchart illustrating a method for retrieving projection information associated with each X-ray source from summed projection information acquired during simultaneous illumination, using source modulation pattern signals and summed projection signal correlation analysis, according to an embodiment.

FIG. 14 presents a method 1400 of extracting projection information associated with each source from combined (summed) projection data acquired with simultaneous illumination by a plurality of sources. In the left column of FIG. 14, calibrations steps 1410 are presented that correspond to calibration data acquisition. For each cell in a detector array, the individual cell response 1418 is determined as a function of selected source modulation parameters. This calibration process, taking place on an individual source basis, may include air scans as well as scans performed with specific calibration object in the beam, 1414.

In the right column of FIG. 14, processing proceeds as follows, and is described for fan-beam projection with vertices at the sources. Projection data are acquired over time from simultaneous exposure by two or more radiation sources, 1422. For each projection, from the calibration data, for each source and for each cell, a corresponding air and calibration scan data cell response(s) are retrieved 1430 and thus projection source modulation vectors are formed 1440, one per radiation source, corresponding to the respective source time evolutions. For each projection, local correlation analysis 1450 is then performed to decompose the summed projection data corresponding to the simultaneous illumination by the active source set onto sets of projection data. One data set 1460 is associated with each of the simultaneously active sources. Each of those projection data sets is then corrected for specific source modulation parameter values, using the appropriate source vectors as calculated previously, 1470. The outcome of this process is then a set of source-modulation-corrected, source-labeled projection data 1480, from which CT image reconstruction can proceed as is known in the art. It is noted that the steps on the right column of FIG. 14 that are within a dashed ellipse 1490 may also be performed as part of the calibration steps; that is, they could as well appear in the left column of FIG. 14.

It is now stated what data set each source representative vector, as discussed in the context of FIG. 13, is correlated with. In the case of a "third-generation"-like geometry, as illustrated for example in FIG. 6, for each source and each detector cell, the distance of the origin to the ray joining the source to the detector cell remains constant during the gantry rotation: Accordingly, and as in the above description, the source representative vector is locally correlated with columns in the output sinogram, one column per detector cell and one row per gantry position. The correlation is local, that is involves only a subset of rows/gantry positions, since it relies on the relatively slow variations of the line-integrals low- and middle-frequency components.

In the case where the relative position of the sources with respect to the detector changes with time, as is the case for the CT geometries with a flying detector and when $\omega d \ne \omega s$, it may be advantageous to rebin the output sinogram so that one-dimensional sinogram lines contain data that correspond to time variations of the active sources.

The local correlation method by itself may be complemented as is now described.

X-ray tubes have long had the capability, in certain designs, to "pinch" the electron beam down to a negligible quantity very rapidly. This is done for example in "gridded tubes," where grids or focusing cups are provided and varying voltages can be applied to these elements. For illustration, when a negative voltage is applied, the electrons are repelled by the cup or grid and thus no electron flows exists between the cathode and the anode; and thus no X-rays are emitted when the tube is pinched off. This gridding mechanism enables turning the emissions of an X-ray tube on and off very rapidly; such that tube emissions can be switched in a few micro-seconds.

Figure 15:
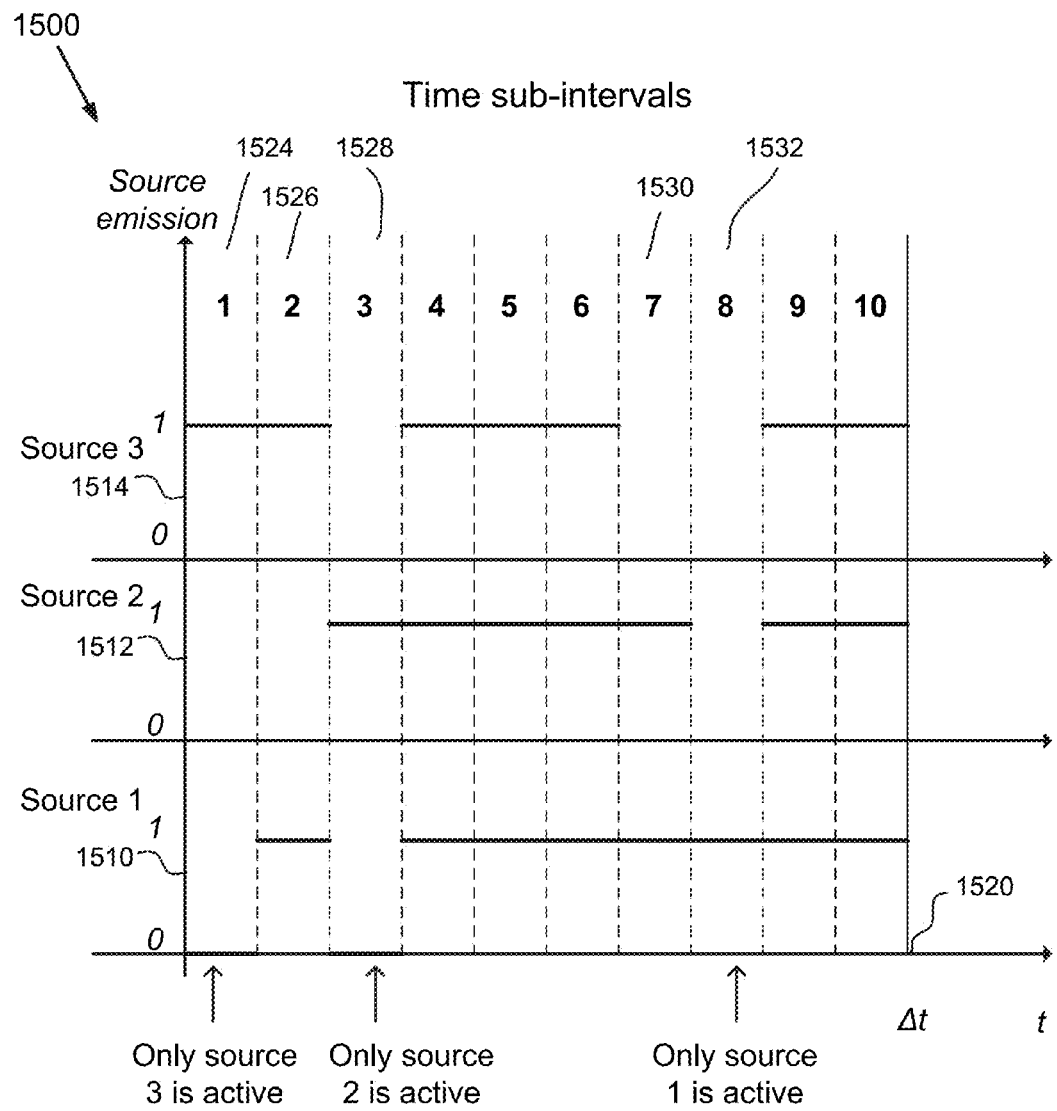
FIG. 15 illustrates the use of tube gridding during a sampling interval $\Delta t$ in identifying components of the summed projection signal associated with each of three simultaneously active radiation sources, according to an embodiment.

FIG. 15 schematically illustrates 1500 applications of tube gridding to simultaneous X-ray exposure applications. In the particular case illustrated, three sources 1510, 1512, and 1514 are simultaneously in view of the detector, and thus available to simultaneously irradiate the patient or object to be imaged. A nominal time interval $\Delta t$ 1520 corresponding to the usual time acquisition of one projection data set is subdivided in a number of sub-intervals 1524, 1526, 1528. For simplicity of development, equal sub-intervals are considered; naturally this need not be the case in general. During these sub-intervals, the various radiation sources are pinched on and off and sub-interval readings are obtained at the detector in such a manner that (i) most of the time the sources are simultaneously active; and (ii) there exists at least one time sub-interval for each source during which only that particular source is active. In the example illustrated, in sub-time intervals 1 1524, 3 1528, and 8 1532 only sources 3, 2 and 1 respectively are active. Whether all the sources are active simultaneously in the other time intervals is a function of design. In the embodiment of the figure, in time intervals 2 1526 and 7 1530, only two sources are active.

Thus, at the cost of an increased sampling rate, sub-projection signals can be acquired that are representative of the signals and individual line-integral terms $\hat{l}$ to be associated with each of the simultaneously active sources. These sub-projection signals can then serve as input to the correlation analysis process, to improve identification of the components of the total projection signals (that is, as obtained after integration over the entire sampling time interval $\Delta t$) that are to be assigned to each source.

These preliminary estimates of the line-integrals may also be used to refine the source-representative vectors: The total beam attenuation along a given line-integral being given by:

$$I = I_0 \exp(-\hat{l}), \quad (11)$$

It is possible to model (particularly in medical imaging): $\hat{l} = L \times \mu_{water}(E_{Eff})$ as the product of an estimated path length L through a water tissue at a specific effective energy $E_{Eff}$. By passing the source output spectrum through this "body filter" as illustrated for example in FIG. 11 (for a specific "phantom" object) we obtain an improved estimate for the total intensity reaching a particular detector cell from a specific source at an instant in time. Therefore by applying this filter at each time sample of the source-representation vector, an "effective" source-variation vector as seen by the detector can be determined iteratively.

By correlation analysis we mean any of various techniques as known in the art that are useful in identifying a signal component that is similar to a calibration signal. The term calibration refers to either data acquired during specific calibration steps, or data acquired under specific controlled circumstances; such as when only one radiation source is active at a time. Correlation techniques as known in the art include Fourier analysis; Vector orthogonal projection analysis, including Gram-Schmidt orthogonalization or partial Gram-Schmidt orthogonalization; statistical analysis, including Bayesian methods with prior-information, and principal component analysis and variants thereof; Cholesky decomposition; Least-squares, weighted least-squares analysis; Canonical correlation analysis; Regression analysis; and other as known in the art. For instance, in general least-square correlation analysis, a merit function is formed as:

$$\chi^2 = \sum_{i=q}^{i=r} \left[ \frac{y_i - \sum_{k=1}^{m} a_k \hat{G}_s^{k,i}(x_i)}{\sigma_i} \right], \quad (12)$$

where the $\hat{G}_s^{k,i}$ are the source control vectors associated with each individual source $S_k$ to be correlated to, $y_i$ are the summed projection data, and $\sigma_i$ is the measurement error associated with $y_i$ (or an estimate thereof; if unknown, set to 1); and $x_i$ is the time associated with measurement $y_i$. Minimization of this expression leads to an estimate for the coefficients $a_k$. In Eq. (12) it is understood that the range of summation $i=q$ to $i=r$ indicates that a local correlation is performed. Further, the output of the correlation may be used for the entire length $(r-q+1)$ of the correlated vectors, or for just the one row considered. That is, the correlation may be considered valid for several views/rows; or may be recalculated for each view/row (as well as for each detector cell/sinogram column). In the following, for simplicity of description the bracket notation <|> is used to denote the output of the correlation process.

Under the conditions described above, the source control vectors then each correspond to a column in the sinogram data (native or rebinned) for a given tomographic slice of interest. By correlating the summed sinogram data $(I_i^j)_{i=1,\ldots,N; j=1\ldots,M} = (P_i^j)_{i=1,\ldots,N; j=1\ldots,M}$ with the (column) source-modulation vectors $$\hat{G}_s^{k,j} = \frac{G_s^{k,j}}{\|G_s^{k,j}\|}, j = 1, \ldots, M,,$$

one obtains, for each row i:

$$\overline{P}_i^{k,j} = F[\langle P_s^{k,j} | \hat{G}_s^{k,j} \rangle \hat{G}_s^{k,j}], k=1,\ldots,K; j=1,\ldots,M, \quad (13)$$

Where $\overline{P}_i^{k,j}$ represents the correlated term for data point ($P_i^j$) associated with source k and in Eq. (13) the functional F[.] represents the process of extracting element indexed by i from the correlation vector $\langle P_s^{k,j} | \hat{G}_s^{k,j} \rangle \hat{G}_s^{k,j}$, or a subset of elements for an index range (for i) over which the local correlation output is considered valid. In the above equation, we have temporarily renamed the summed projection data P. The residual sinogram data elements can then be expressed by subtracting the sum of correlated terms:

$$\tilde{P}_i^j = P_i^j - \Sigma_{k=1}^{k=K} \overline{P}_i^{k,j}, i=1,\ldots,N; j=1,\ldots,M \quad (14)$$

The above methods can be used by themselves, or as a regularization step to the linear inverse problem discussed in previous sections. This is now discussed in more details in the context of a multisource CT system with one rotating gantry, the system satisfying equidistribution condition (C.4). When K sources are simultaneously active and over a full rotation of a CT gantry, M projections are acquired each providing N measurements, the inverse problem that necessarily precedes image reconstruction can be formulated as:

$$[I]_{M \times N} = [A]_{M \times N, M \times N} [ELI]_{M \times N}, \quad (15)$$

where as described above, $[I]_{M \times N}$ is the vector of measured projection data (intensities), $[ELI]_{M \times N}$ is the vector of the exponentials of the negative of the unknown line-integrals, and the matrix A is a (large) square matrix which is quite sparse, since on each matrix row only up to K terms are non-zero. The coefficients of matrix A are given by the source intensities. Since matrix A is square, sparse, and some of the coefficients are under system control, it is always either invertible or nearly invertible—that is, amenable to regularization, for instance in the form of Tikhonov regularization, as known in the art (Briefly, Tikhonov regularization consists of replacing matrix $A^T A$ with $A^T A + \alpha I$ in solving the inverse problem).

There exist many ways to formulate an inverse problem such as this pre-reconstruction inversion. In a conventional least-squares approach, the inverse problem is written as:

$$\min_{ELI} \|[I]_{M \times N} - [A]_{M \times N, M \times N} [ELI]_{M \times N}\|^2. \quad (16)$$

The least-squares problem above can be regularized by the addition of various penalization (or "constraint") terms. From the discussion above, the correlation analysis constraints can be formulated as (where in Eq. (17) for notational simplicity the constraints are expressed in terms of vectors (along row/view index i):

$$\min_{ELI, \beta} \left\{ \begin{array}{l} \|[I]_{M \times N} - [A]_{M \times N, M \times N}[ELI]_{M \times N}\|^2 + \\ \beta \sum_{i=1}^{i=N} \left\| I_j - \sum_{k=1}^{k=K} \beta_s^{k,i} \hat{G}_s^{k,i} \right\|^2 \end{array} \right\}. \quad (17)$$

In the limit case where correlation with each of the simultaneously active sources is performed for each row in turn (that is, the output of a given correlation is retained for only one measurement, rather than from a local vector of measurements), then the constraint also involves a sum over all projection indices i,j:

$$\min_{ELI, \beta} \left\{ \begin{array}{l} \|[I]_{M \times N} - [A]_{M \times N, M \times N}[ELI]_{M \times N}\|^2 + \\ \beta \sum_{j=1}^{j=M} \sum_{i=1}^{i=N} \left\| [[A]_{M \times N, M \times N}[ELI]_{M \times N}]_{i,j} - \sum_{k=1}^{k=K} \overline{P}_i^{k,j} \right\|^2 \end{array} \right\}, \quad (18)$$

\where $[[A]_{M \times N, M \times N}[ELI]_{M \times N}]_{i,j}$ represents the (i,j) element of column vector $[A]_{M \times N, M \times N}[ELI]_{M \times N}$ (under certain indexing conventions calculated as i×M+j).

In equations (17) and (18), the minimization is over the line-integral negative-exponential terms as well as the weight/coefficient β. As is known in the art, the regularized problem can be stated and solved numerically in a number of different ways; the expression above being typical of least-squares minimization. Of course, different norms could be used as well. The coefficient β weights the contributions of the regularization terms associated with the source-correlations versus the match of the line-integral terms with the intensity measurements. Numerical solvers include the method of conjugate gradient, for example.

In Eq. (18), the match to the individual (gridding-obtained) line-integrals is performed through the sum associated with a given projection measurement. It is clear that one could rewrite equation (18) to enforce as a constraint a match to the individual line-integrals instead. The corresponding equation involves rebinning the ELI terms and is not detailed here.

As described above X-ray tube gridding and use of specific gridding control timing sequence enable the acquisition of projection data sets associated with each of the otherwise simultaneously active sources. Such apparatus and methods then provide initial line-integral estimates and projection data set vectors that can serve as input to the process of summed projection data correlation processing. Thus, denoting $P_{e,i}^{k,j}$ the corresponding source-labelled projection estimates, and by B( ) a projection processing operator (not necessarily linear), we may add a term to the general inverse problem of equation (18) above:

$$\delta \Sigma_{j=1}^{j=M} \Sigma_{i=1}^{i=N} \|[[A]_{M \times N, M \times N}[ELI]_{M \times N}]_{i,j} - \Sigma_{k=1}^{k=K} B (P_{e,i}^{k,j})\|^2 \quad (19)$$

Equation (19) serves to ensure that the extracted signal $ELI_i^j$ do not deviate too much from the noisy individual measurements $P_{e,i}^{k,j}$. The B( ) operator maybe in some embodiments a smoothing operator so that the estimates $P_d^{k,j}$ are not forced to match random noise variations in the $P_e^{k,j}$. In another embodiment, B( )=Id( ) is the identity operator. The constant δ serves to weight the relative contribution of term (19) to the overall inversion problem (18). It is understood (but not shown in equation (19)) that the smoothing operator B( ) may also be applied across rows of the detector: anatomical low- to mid-frequency information is known to vary relatively slowly along the z-axis; therefore it is possible to perform a local smoothing operation with respect to the rows (that is, row-to-row, such as row averaging or weighted averaging over a limited distance) to capture the relevant low and mid-frequency information.

As in the context of Eq. (18), one can impose as a constraint a match to the individual line-integral estimates obtained via gridding, rather than a constraint on the sum of the individual line-integral terms associated with a single measurement. The corresponding constraint term would then be written as:

$$\delta \Sigma_{j=1}^{j=M} \Sigma_{i=1}^{i=N} \Sigma_{k=1}^{K} \|R(ELI_i^j)_{i,j} - B(P_{e,i}^{k,j})\|^2. \quad (20)$$

where R( ) is a rebinning operator.

Considering a dual-drum geometry with a flying detector, as in FIGS. 8A and 8B, it has been shown (G. M. Besson, Medical Physics 42, 2668 (2015); doi: 10.1118/1.4918328) that for such a system with a total of $N_S$ sources and K sources simultaneously in view of the detector, the flying detector angular velocity ratio with respect to the source drum angular velocity can be as high a:

$$\frac{\omega_d}{\omega_s} = K. \quad (21)$$

Accordingly, tomographic data acquisition can also be performed in 1/K the time required by a standard CT system with a one source conventional CT gantry rotating at $\omega_s$ radians per seconds.

To maintain the total number of projection acquired per effective data acquisition rotation, it is thus necessary to increase the detector sampling rate in proportion to K. Thus if a third-generation system samples data with each projection corresponding to a $\Delta t$ projection acquisition time, the dual-drum system operating at maximum speed (for acquisition of a full set of projections, with uniform angular view sampling) will sample the projections in a time intervals equal to $$\frac{\Delta t}{K}.$$

In such a system with $\omega_d = K \times \omega_s$, each line integral path through the object is sampled only once (with quarter offset), respectively twice (without quarter offset). The detector acquires $N_V$ summed projection data sets per rotation, each data set corresponding to the data summed for up to K sources in view of the detector. In this configuration, this corresponds to $N_V \times K$ source-based fan-beam projections, and thus a total of $N_V \times K \times M$ line integrals. This configuration thus defines a sampling of the tomographic plane comprising K times more line-integrals; these being acquired in a summed configuration, and associated to only $N_V \times M$ measurements. Thus the associated problem appears significantly underdetermined.

However, using the source-modulation approach described above, it is possible to recover individual line-integral data for $N_V \times M$ lines, which is what a third-generation CT system operating at $\omega_s$ gantry rotation and $\Delta t$ projection sampling time would acquire.

This local recovery of the data is performed as described below in illustrative embodiments. Many variations on the precise method described below are possible, and are understood to be within the scope of the present invention.

We denote by $\delta t_i$, $i=1, \ldots, K$ the K consecutive equal (for simplicity of exposition) time intervals that make up a time interval $\Delta t$. Hence $$|\delta t_i| = \left|\frac{\Delta t}{K}\right|.$$

Figure 16:
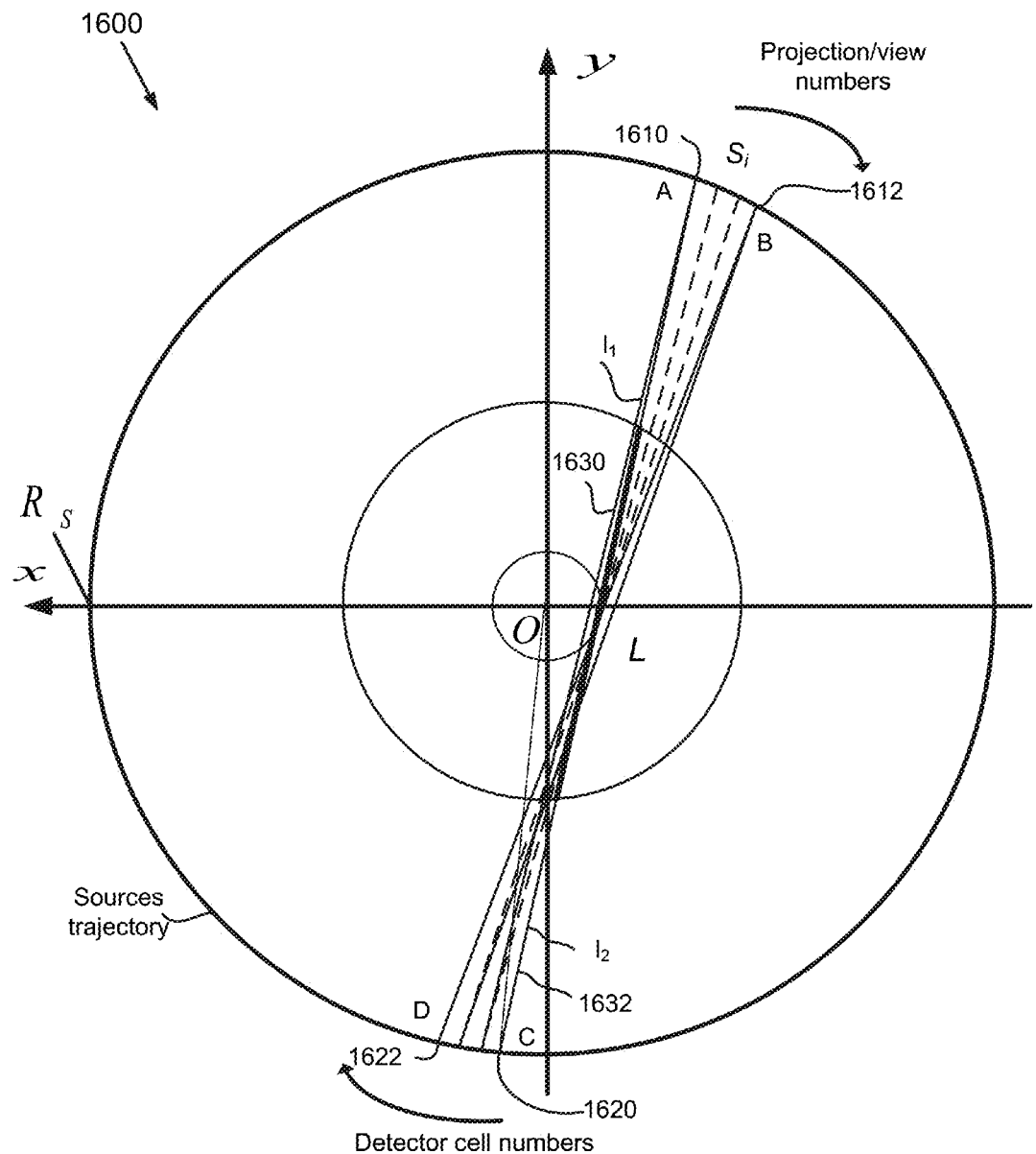
FIG. 16 describes schematically the sampling associated with a given sampling interval time $\Delta t$ in a conventional CT system and the sub-sampling obtained in a dual-drum CT system operating at higher data acquisition speed.

The sampling geometry 1600 is illustrated in FIG. 16 for K=3; where the dimensions are not to scale, and the blurring effect associated with the sampling interval $\Delta t$ has been magnified for the purpose of explanation. During this sampling interval, the source in a conventional CT system, and one of the K sources in the system of the present invention travels from point A 1610 to point B 1612. In conventional CT, the associated detector cell corresponding to the sampling of "one line-integral" travels from location C 1620 to location D 1622. In the dual-drum CT system of the present invention, the sources travel at the same angular velocity $\omega_s$. However during the source travel time corresponding to the arc A to B, the flying detector, which is moving at angular speed $\omega_d = K \times \omega_s$, is sampled K times. Thus the arc CD is swept K times during the interval $\Delta t$ by K successive cells on the detector (each cell sweeping in turn from point C to point D in a time interval $$\delta t_i = \frac{\Delta t}{K}\Big),$$

and the K samples are associated with the same total area $\Omega$ within the object of interest as that swept in a conventional system. This total object area $\Omega$ is delimited by lines $l_1$ 1630 and $l_2$ 1632 in FIG. 16. Further, the total number of photons detected (and associated with individual source in the set of K sources) and represented by the K samples, is the same as that measured in the time interval $\Delta t$ in a conventional system with one source (assuming all other factors constant).

Relabeling the line-integrals for the description, a given source $S_i$ traces during $\Delta t = K \times |\delta t_i|$ paths for K line integrals $L_i^j$; $i=1, \ldots K$; $j=1, \ldots K$. This set of K lines integral for one of the sources are all associated with, and correspond to the same object area $\Omega$, as the data acquired for one line-integral in a conventional CT system. Thus now considering the K simultaneously active sources, we are led to a system of equations with $K^2$ unknowns:

$$\begin{bmatrix} m_1 \\ \vdots \\ m_K \end{bmatrix} = \begin{bmatrix} I_{01}^1 & I_{0K}^1 & & & \\ & & 0 & 0 & \\ & & & & \\ & 0 & 0 & & \\ & & & I_{01}^K & I_{0K}^K \end{bmatrix} \begin{bmatrix} L_1^1 \\ \vdots \\ L_K^1 \\ L_1^K \\ \vdots \\ L_K^K \end{bmatrix} \quad (S1)$$

$$= [I]_{K,K^2} \begin{bmatrix} L_1^1 \\ \vdots \\ L_K^1 \\ L_1^K \\ \vdots \\ L_K^K \end{bmatrix}$$

Figure 17:
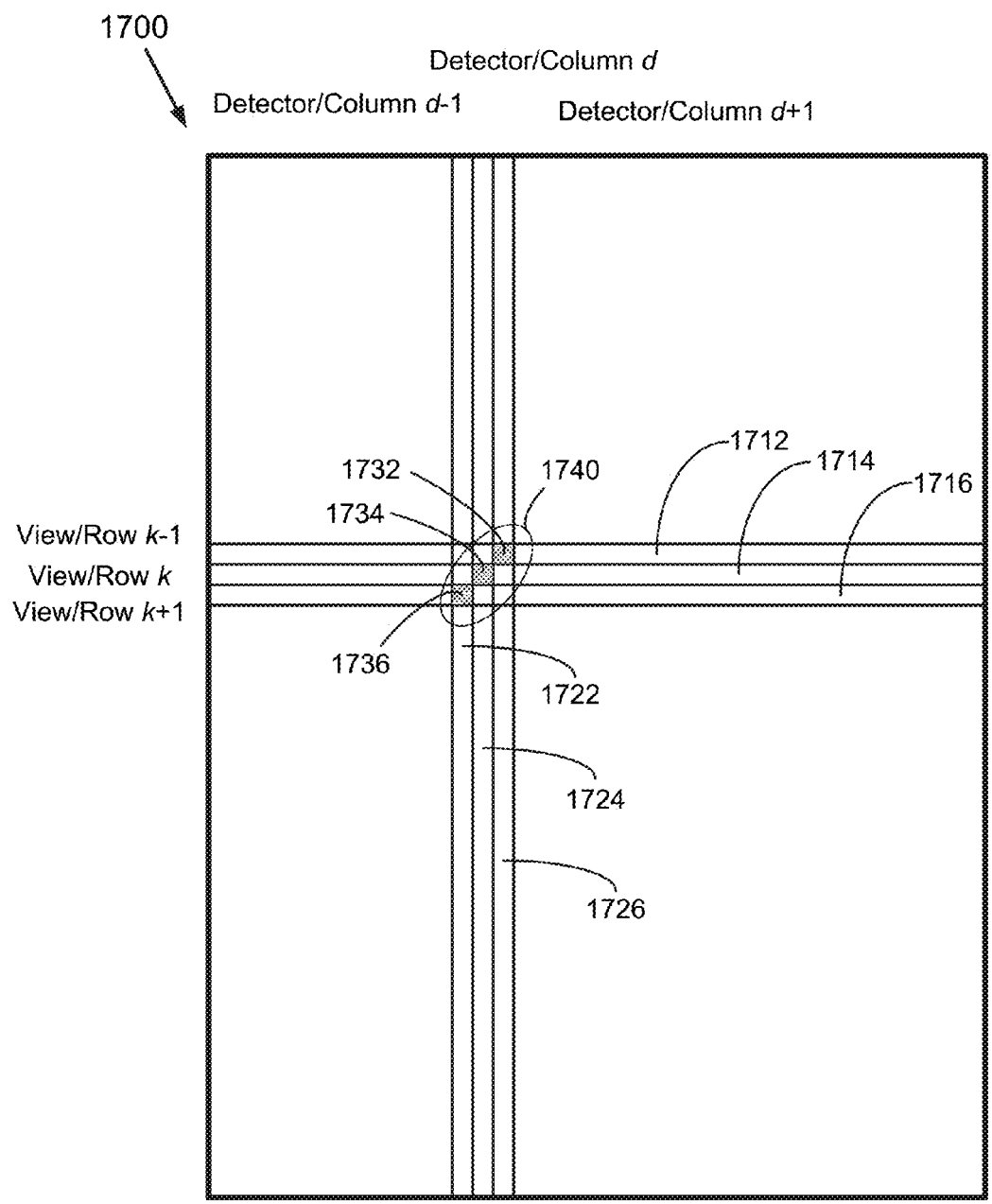
FIG. 17 shows the various rows and detector cells involved in the sub-sampling of a line-integral, as obtained for a dual-drum CT system with three simultaneously active radiation sources.
Figure 18:
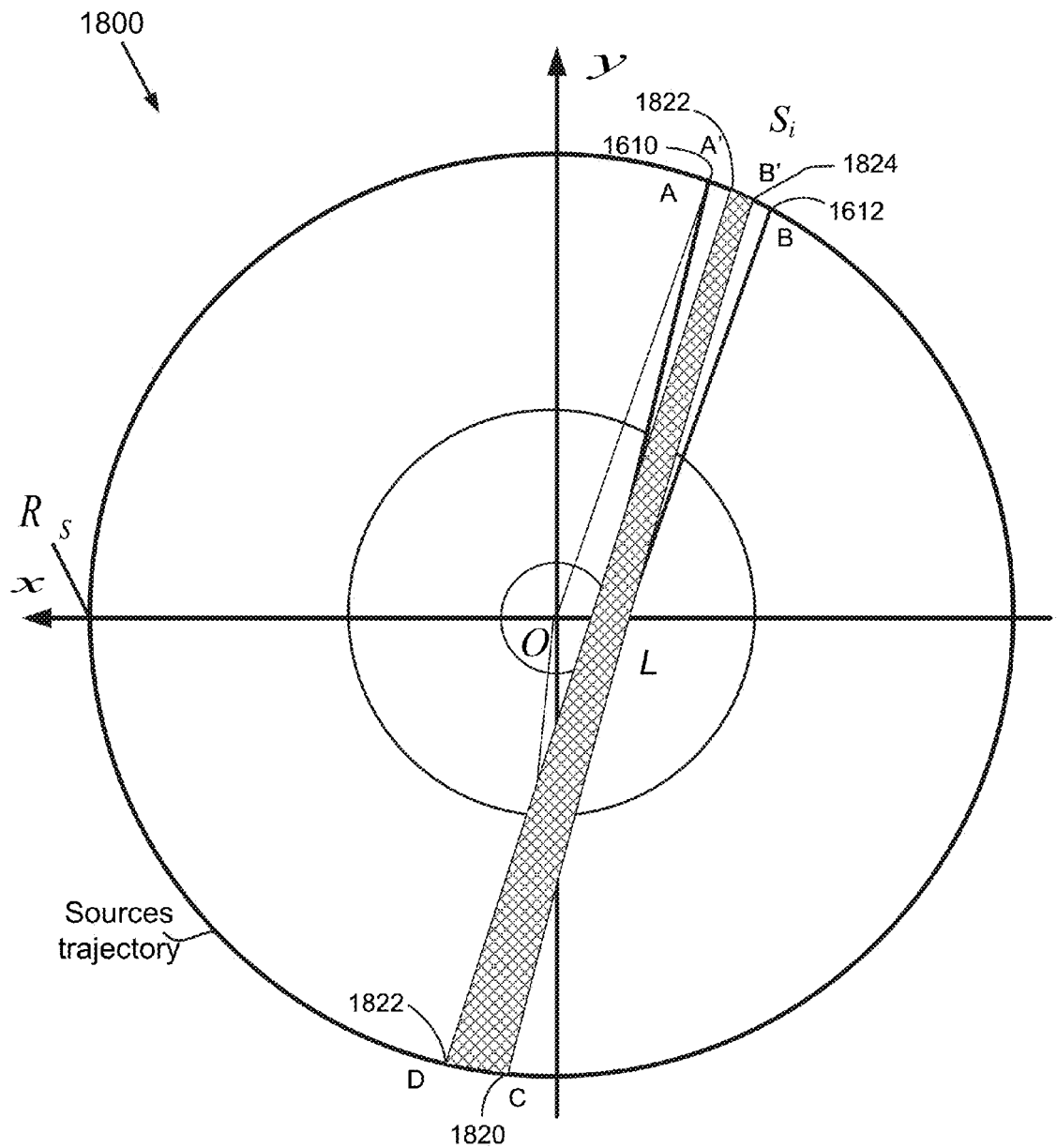
FIG. 18 depicts the sub-sampling of the object obtained with the second of the three detector cells of a dual-drum CT system with three simultaneously active radiation sources, sweeping a sub-area of the object area swept by a single-source conventional CT system.

In the system (S1), each of the K measurements $m_i$, $i=1, \ldots K$ is associated with one of the successive detector cell that sweeps the arc CD in the corresponding time intervals $\delta t_i$. In other words, these measurements are associated to successive rows 1712, 1714, 1716 in the summed projection sinogram and laterally offset columns 1722, 1724, 1726, as indicated schematically, 1700, in FIG. 17 for a system with K=3. Thus the K=3 samples indicated by cross-hatched marks 1732, 1734, and 1736 inside ellipse 1740 are all related to sub-areas of object area $\Omega$. This is shown 1800 in FIG. 18 for the second of the three samples acquired by the flying detector in the case of a system with K=3: the cross-hatched area 1812 corresponds to the central sub-arc A' 1822 to B' 1824 from arc 1610 to 1612 shown in FIG. 16. The corresponding detector cell however travels the full arc range C 1820 to D 1822 during the sub-sampling time interval $|\delta t_2|=\Delta t/3$.

To solve this a-priori underdetermined system of equation locally, we identify $L_i=L_i^1 \sim L_i^j$ for each source $S_i$ i=1, ..., K and j=1, ... K. This is an approximation valid in the sense that all line integrals pertain to the same area Ω (for a given source i). Accordingly, under this approximation the system (S1) may be rewritten as a system of equations in K unknowns:

$$\begin{bmatrix} m_1 \\ . \\ m_K \end{bmatrix} = \begin{bmatrix} I_{01}^1 & . & I_{0K}^1 \\ . & . & . \\ I_{01}^K & . & I_{0K}^K \end{bmatrix} \begin{bmatrix} L_1 \\ . \\ L_K \end{bmatrix} \quad (S2)$$

$$= [I]_{K,K} \begin{bmatrix} L_1 \\ . \\ L_K \end{bmatrix}.$$

If the sources parameters do not vary in time, then system (S2) is non-invertible or at least severely ill-conditioned, since the rows of the K-by-K $[I]_{K,K}$ matrix are proportional. To locally invert such a system, we introduce, in one embodiment, sources modulations in the following manner.

During each of the time intervals $\delta t_i$ we pinch-off the beam for one of the K sources, source $S_i$, in turn. Assuming for simplicity of description, that all the other source parameters are equal, system (S2) can be written as (with $I_0$ the sources common air output):

$$\begin{bmatrix} m_1 \\ . \\ m_K \end{bmatrix} = I_0 [J_K - I_K] \begin{bmatrix} L_1 \\ . \\ L_K \end{bmatrix}, \quad (S3)$$

where $J_K$ and $I_K$ represent the square matrices of size K-by-K with all entries equal to 1 and the identity matrix with ones on the main diagonal and zeroes elsewhere, respectively. Hence:

$$[J_K - I_K] = \begin{bmatrix} 0 & 1 & ... & 1 \\ \vdots & & \ddots & \vdots \\ 1 & ... & 1 & 0 \end{bmatrix}. \quad (S4)$$

Matrix $[J_K-I_K]$ is known in algebra to be invertible and diagonalizable, with $$det([J_K-I_K])=K \times (-1)^{K-1}.$$

Thus as described above X-ray tube gridding and use of specific gridding control timing sequence enable the acquisition of projection data sets from which estimates for the individual line-integrals can be recovered locally from summed measurements, in a dual-drum CT system effectively rotating at K times the angular velocity of a conventional one-source CT system.

In specific embodiments, CT systems with higher spatial resolution can also be obtained. Indeed, by rotating the detector drum in a dual-drum system at an angular velocity less than the maximum enabling complete data set acquisition, Eq. (21), sub-samplings of the object area associated to sampling by a single-source CT system of the present state-of-the-art are obtained. These sub-sampling in turn provide higher object sampling, leading to higher image spatial resolution.

This sub-sampling can also be combined with distributing the required exposure power in between the sub-set of sources. Reduced tube power enables the use of smaller size tube focal spot, and thus reduce the associated blurring, further leading to higher spatial resolution.

The advantages of the above described apparatus embodiments, improvements, and methods should be readily apparent to one skilled in the art, as to enabling the design of computed tomography systems acquiring full sets of projection data and optimized for both speed of data acquisition and efficiency of design with respect to the number of radiation sources employed. Additional design considerations may be incorporated without departing from the spirit and scope of the invention. It should thus be noted that the matter contained in the above description and/or shown in the accompanying drawings should be interpreted as illustrative and not in a limiting sense. Accordingly, the following claims are intended to cover all generic and specific features described herein, as well as all statements of the scope of the present methods, and systems which, as a matter of language, might be said to fall therebetween.

The invention claimed is:

1. A computed-tomography (CT) X-ray scanner comprising:
    A plurality of X-ray sources mounted to a first rotatable gantry;
    an X-ray detector array disposed for illumination by the X-ray sources, the detector array comprising at least M detector cells;
    apparatus for supporting a patient in an imaging zone between the X-ray sources and the X-ray detector array;
    a control and image processing system coupled to receive X-ray data from the X-ray detector array, the control and image processing system comprising at least one digital processor and a memory, and
    machine readable instructions in the memory comprising:
        Machine readable instructions configured to, when executed by the at least one processor, energize an integer K of the X-ray sources simultaneously while rotating the first rotatable gantry and recording a plurality of measurements N at each gantry position P, at least a subset of the plurality of measurement corresponding to a sum of line integrals $L_{kmp}$ of radiation from two or more of the K X-ray sources as attenuated by passage through the imaging zone to a cell of the detector array, the measurements designated $N_{mp}$;
    wherein a first measurement $N_{mp1}$ at a first gantry position $P_1$ and a second measurement $N_{mp2}$ at a second gantry position $P_2$, $P_1$ and $P_2$ being different, each measurement $N_{mp1}$ and $N_{mp2}$ representing a sum of line integrals comprising a line integral of attenuation of radiation along a same line L; and
    inversion machine readable instructions configured to determine an individual line integral of attenuation along the line L from the measurements comprising sums of line integrals of attenuation along the line L.

2. The scanner of claim 1 wherein the K energized radiation sources are disposed across an arc defining a central angle of no more than π radians of the gantry.

3. The scanner of claim 2 wherein the machine readable instructions are configured to determine a plurality of line integrals of attenuation of radiation along multiple distinct lines L, and further comprising machine readable instructions configured to reconstruct a three-dimensional, model of attenuation of radiation in the imaging zone from the line integrals of attenuation of radiation along the multiple distinct lines L.

4. The scanner of claim 2, wherein the detector array describes an arc, the arc locally having a curvature center within the imaging zone and a central angle approximately π radians plus two times a system fan angle.

5. The scanner of claim 4 wherein the X-ray sources are disposed along an arc of less or equal to π radians minus twice the system fan angle.

6. The scanner of claim 2 wherein the detector array is disposed upon a second rotatable gantry, and wherein the second rotatable gantry has a slot through which an X-ray source selected from the plurality of the X-ray sources may illuminate the imaging zone.

7. The scanner of claim 1 further comprising reconstruction machine readable instructions in the memory, the machine readable instructions configured to, on execution by a processor, use the individual line integrals of a plurality of lines L to reconstruct a three dimensional map of attenuation in the imaging zone, wherein the reconstruction machine readable instructions are configured to execute after the inversion machine readable instructions.

8. A method of performing computed-tomography (CT) X-ray scanning comprising:
  simultaneously generating X-ray radiation from a plurality of K X-ray sources, the X-ray sources being mounted to a first rotatable gantry;
  positioning the gantry at a position P1 and measuring X-rays received at M detector cells of an X-ray detector array disposed for illumination by the X-ray sources to generate a plurality of measurements N1;
  rotating the first rotatable gantry to a second position P2 and recording a second plurality of measurements N2;
  where measurements N1 and N2 each corresponding to a sum of line integrals $L_{kmp}$ of radiation from two or more of the K X-ray sources as attenuated by passage through an imaging zone to a cell of the detector array, and
  wherein a first measurement Nmp1 in measurements N1 and a second measurement Nmp2 in measurements N2 represent a sum of line integrals comprising a line integral of attenuation of radiation along a same line L in both Nmp1 and Nmp2; and
  determining an individual line integral of attenuation along the line L from the measurements comprising sums of line integrals of attenuation along the line L.

9. The method of claim 8 further comprising using the individual line integrals of a plurality of lines L to reconstruct a three dimensional map of attenuation in the imaging zone.

10. The method of claim 9 wherein the K energized radiation sources are disposed across an arc of no more than π radians of the gantry.

11. The method of scanning of claim 9, wherein the detector array describes an arc, the arc locally having a curvature center within the imaging zone and a central angle approximately π radians plus two times a system fan angle, and the X-ray sources are disposed along an arc of less or equal to π radians minus twice the system fan angle.

12. The method of claim 9 wherein the detector array is disposed upon a second rotatable gantry, and wherein the second rotatable gantry has a slot through which an X-ray source of the X-ray sources illuminate the imaging zone.

13. A computed-tomography (CT) X-ray scanner comprising:
  A plurality of X-ray sources mounted to a first rotatable gantry, wherein the X-ray sources are adapted for modulation;
  an X-ray detector array disposed for illumination by the X-ray sources, the detector array comprising at least M detector cells;
  apparatus for supporting a patient in an imaging zone between the X-ray sources and the X-ray detector array;
  a control and image processing system coupled to receive X-ray data from the X-ray detector array, the control and image processing system comprising at least one digital processor and a memory, and
  machine readable instructions in the memory comprising:
    machine readable instructions configured to, when executed by the at least one processor, energize an integer K of the X-ray sources simultaneously, while modulating the K radiation sources in known ways at known frequencies, while rotating the first rotatable gantry and recording a plurality of measurements N at each gantry position P, at least a subset of the plurality of measurement corresponding to a sum of line integrals Lkmp of radiation from two or more of the K X-ray sources as attenuated by passage through the imaging zone to a cell of the detector array, the measurements designated Nmp;
  wherein a first measurement Nmp1 at a first gantry position P1 and a second measurement Nmp2 at a second gantry position P2, P1 and P2 being different, each measurement Nmp1 and Nmp2 representing a sum of line integrals comprising a line integral of attenuation of radiation along a same line L, the measurements captured at a rate greater than a frequency of the modulation of the X-ray sources; and
  inversion machine readable instructions configured to determine an individual line integral of attenuation along the line L from the measurements comprising sums of line integrals of attenuation along the line L, the inversion machine readable instructions constrained by the relative intensities of the known modulation of the radiation sources.

14. A method of performing computed-tomography (CT) X-ray scanning comprising:
  simultaneously generating modulated X-ray radiation from a plurality of K X-ray sources, the X-ray sources being mounted to a first rotatable gantry;
  positioning the gantry at a position P1 and measuring X-rays received at M detector cells of an X-ray detector array disposed for illumination by the X-ray sources to generate a plurality of measurements N1;
  rotating the first rotatable gantry to a second position P2 and recording a second plurality of measurements N2;
  where measurements N1 and N2 each corresponding to a sum of line integrals Lkmp of radiation from two or more of the K X-ray sources as attenuated by passage through an imaging zone to a cell of the detector array, and
  wherein a first measurement Nmp1 in measurements N1 and a second measurement Nmp2 in measurements N2 represent a sum of line integrals comprising a line integral of attenuation of radiation along a same line L in both Nmp1 and Nmp2; and
  determining an individual line integral of attenuation along the line L from the measurements comprising sums of line integrals of attenuation along the line L and known modulations of the K radiation sources.

15. The method of claim 14 further comprising using the individual line integrals of a plurality of lines L to reconstruct a three dimensional map of attenuation in the imaging zone.

16. The method of claim 15 wherein the K energized radiation sources are disposed across an arc defining a central angle of no more than π radians on the gantry.

17. The method of claim 14 wherein the known modulation of the radiation sources is used as a constraint in determining an individual line integral of attenuation along the line L from the measurements.

18. The method of claim 17 wherein the known modulation of the radiation sources is selected from tube current modulation, beam filter modulation, peak voltage modulation, beam pinch modulation, and spot size modulation at the radiation sources.

19. A computed-tomography (CT) X-ray scanner comprising:
 a plurality of X-ray sources mounted to a first rotatable gantry, wherein the X-ray sources are adapted for beam-pinched gating;
 an X-ray detector array disposed for illumination by the X-ray sources, the detector array comprising at least M detector cells;
 apparatus for supporting a patient in an imaging zone between the X-ray sources and the X-ray detector array;
 a control and image processing system coupled to receive X-ray data from the X-ray detector array, the control and image processing system comprising at least one digital processor and a memory, and
 machine readable instructions in the memory comprising:
  machine readable instructions configured to, when executed by the at least one processor, alternately pulsing an integer K of the beam-pinch gateable radiation sources, while rotating the first rotatable gantry and recording a plurality of measurements N at each gantry position P, at least a subset of the plurality of measurement corresponding to a sum of line integrals Lkmp of radiation from two or more of the K X-ray sources as attenuated by passage through the imaging zone to a cell of the detector array, the measurements designated Nmp;
 wherein a first measurement Nmp1 at a first gantry position P1 and a second measurement Nmp2 at a second gantry position P2, P1 and P2 being different, each measurement Nmp1 and Nmp2 representing a sum of line integrals comprising a line integral of attenuation of radiation along a same line L; and
 inversion machine readable instructions configured to determine an individual line integral of attenuation along the line L from the measurements comprising sums of line integrals of attenuation along the line L, the inversion machine readable instructions constrained by known pulsing of the radiation sources.

20. The scanner of claim 19 wherein at least some measurements are performed sufficiently quickly during individual pulses of the radiation sources that measurements during individual pulses provide an estimate of a line integral of attenuation along line L.

21. The scanner of claim 19 wherein the second gantry is rotated while obtaining the measurements.

22. A method of performing computed-tomography (CT) X-ray scanning comprising:
 simultaneously generating known pulses of X-ray radiation from a plurality of K beam-pinch gateable X-ray sources, the X-ray sources being mounted to a first rotatable gantry;
 positioning the gantry at a position P1 and measuring X-rays received at M detector cells of an X-ray detector array disposed for illumination by the X-ray sources to generate a plurality of measurements N1;
 rotating the first rotatable gantry to a second position P2 and recording a second plurality of measurements N2;
 where measurements N1 and N2 each corresponding to a sum of line integrals Lkmp of radiation from two or more of the K X-ray sources as attenuated by passage through an imaging zone to a cell of the detector array, and
 wherein a first measurement Nmp1 in measurements N1 and a second measurement Nmp2 in measurements N2 represent a sum of line integrals comprising a line integral of attenuation of radiation along a same line L in both Nmp1 and Nmp2; and
 determining an individual line integral of attenuation along the line L from the measurements comprising sums of line integrals of attenuation along the line L and known pulses of X-ray radiation from the K radiation sources.

23. The method of claim 22 further comprising using the individual line integrals of a plurality of lines L to reconstruct a three dimensional map of attenuation in the imaging zone.

24. The method of claim 22 wherein the X-ray detector array is mounted on a second rotatable gantry, and further comprising rotating the second gantry while generating the X-ray pulses.

25. The method of claim 23 wherein the step of determining an individual line integral of attenuation along the line L from the measurements comprises a local inversion.

26. The method of claim 25 wherein the local inversion for a first L-bundle is performed on a matrix derived from a set of simultaneous equations having no more rows than sources in view of the detector during acquisition of data associated with the L-bundle.

27. The method of claim 23 wherein the step of determining an individual line integral of attenuation along the line L from the measurements comprises a global inversion.

28. The method of claim 14 wherein the X-ray detector array is mounted on a second rotatable gantry, and further comprising rotating the second gantry while generating the modulated X-ray radiation.

29. The scanner of claim 19 wherein the X-ray detector array is mounted on a second rotatable gantry.

* * * * *